US008409618B2

(12) United States Patent
MacDonald et al.

(10) Patent No.: US 8,409,618 B2
(45) Date of Patent: Apr. 2, 2013

(54) ODOR-REDUCING QUINONE COMPOUNDS

(75) Inventors: John Gavin MacDonald, Decatur, GA (US); Stephanie M. Martin, Woodstock, GA (US); Jaeho Kim, Roswell, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 1610 days.

(21) Appl. No.: 10/955,316

(22) Filed: Sep. 30, 2004

(65) Prior Publication Data
US 2005/0131363 A1 Jun. 16, 2005

Related U.S. Application Data

(63) Continuation-in-part of application No. 10/325,474, filed on Dec. 20, 2002.

(51) Int. Cl.
A61K 9/14 (2006.01)

(52) U.S. Cl. ........................................... 424/489

(58) Field of Classification Search .................. None
See application file for complete search history.

(56) References Cited

U.S. PATENT DOCUMENTS

| | | | |
|---|---|---|---|
| 3,266,973 A | 8/1966 | Crowley |
| 3,338,992 A | 8/1967 | Kinney |
| 3,341,394 A | 9/1967 | Kinney |
| 3,494,821 A | 2/1970 | Evans |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,794,497 A | 2/1974 | Pratt et al. |
| 3,802,817 A | 4/1974 | Matsuki et al. |
| 3,849,241 A | 11/1974 | Butin et al. |
| 3,960,494 A | 6/1976 | Verma et al. |
| 4,049,776 A | 9/1977 | Nicklin et al. |
| 4,100,324 A | 7/1978 | Anderson et al. |
| 4,144,370 A | 3/1979 | Boulton |
| 4,158,822 A | 6/1979 | Wan |
| 4,297,233 A | 10/1981 | Gualanid |
| 4,325,735 A | 4/1982 | Ohta et al. |
| 4,336,027 A | 6/1982 | Tussing |
| 4,340,563 A | 7/1982 | Appel et al. |
| 4,407,960 A | 10/1983 | Tratnyek |
| 4,467,012 A | 8/1984 | Pedersen et al. |
| 4,517,308 A | 5/1985 | Ehlenz et al. |
| 4,556,146 A | 12/1985 | Swanson et al. |
| 4,585,484 A | 4/1986 | Haruta et al. |
| 4,589,876 A | 5/1986 | Van Tilburg |
| 4,601,868 A | 7/1986 | Radel et al. |
| 4,604,313 A | 8/1986 | McFarland et al. |
| 4,622,169 A | 11/1986 | Rickle |
| 4,655,757 A | 4/1987 | McFarland et al. |
| 4,687,478 A | 8/1987 | Van Tillburg |
| 4,701,218 A | 10/1987 | Barker et al. |
| 4,726,844 A | 2/1988 | Greenwood |
| RE32,649 E | 4/1988 | Brandt et al. |
| 4,767,459 A | 8/1988 | Greenwood et al. |
| 4,775,585 A | 10/1988 | Hagiwara et al. |
| 4,783,220 A | 11/1988 | Gamble et al. |
| 4,798,603 A | 1/1989 | Meyer et al. |
| 4,802,473 A | 2/1989 | Hubbard et al. |
| 4,812,492 A | 3/1989 | Eckes et al. |
| 4,836,851 A | 6/1989 | Pawlowski et al. |
| 4,950,264 A | 8/1990 | Osborn, III |
| 4,952,552 A | 8/1990 | Chapman et al. |
| 4,957,553 A | 9/1990 | Koike et al. |
| 4,963,189 A | 10/1990 | Hindagolla |
| 4,969,457 A | 11/1990 | Hubbard et al. |
| 4,988,505 A | 1/1991 | Watanabe et al. |
| 5,000,746 A | 3/1991 | Meiss |
| 5,006,862 A | 4/1991 | Adamic |

(Continued)

FOREIGN PATENT DOCUMENTS

| | | |
|---|---|---|
| EP | 0282287 B2 | 9/1988 |
| EP | 0348978 A2 | 1/1990 |

(Continued)

OTHER PUBLICATIONS

Disperal/Dispal brochure and specifications, Sasol GmbH.*
D & C Green 5—Technical Data, Noveon Hilton Davis Aug. 19, 2004.*
Fionov, Surface Science 507-510: 74-81 (2002).*
Conant and Fieser, J Amer Chem Soc 46: 1858 (1924).*
Nissan Chemicals Snowtex C site, 2007 [downloaded Jul. 11, 2012] [http://www.nissanchem-usa.com/snowtex.php].*
Abstract of Japanese Patent No. JP04255767, Sep. 10, 1992.
Abstract of Japanese Patent No. JP05098185, Apr. 20, 1993.
Search Report and Written Opinion for PCT/US2005/022818, Mar. 22, 2006.
Search Report and Written Opinion for PCT/US2005/022818, 2007, Mar. 22, 2006.
Abstract of Article—*Non-hydrothermal synthesis of copper-,-zinc- and copper-zinc hydrosilicates*, T. M. Yurieva, G. N. Kustova, T. P. Minyukova, E. K. Poels, A. Bliek, M. P. Demeshkina, L. M. Plyasova, T. A. Krieger, and V. I. Zaikovskii, Materials Research Innovations, vol. 5, No. 1, Jun. 2001, pp. 3-11.

(Continued)

*Primary Examiner* — Robert T Crow
*Assistant Examiner* — Thor Nielsen
(74) *Attorney, Agent, or Firm* — Dority & Manning, P.A.

(57) ABSTRACT

An odor control composition that comprises an odor-reducing quinone compound and optionally high surface area particles is provided. In one embodiment, the odor-reducing quinone compound is an anthraquinone having the following structure:

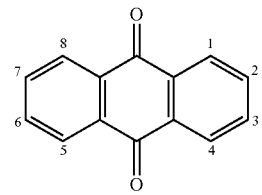

wherein the numbers 1 through 8 refer to optional substitution positions for functional groups. For example, positions 5 through 8 of the anthraquinone may be unsubstituted with functional groups. Examples of such quinone compounds may include those obtained from a dye selected from the group consisting of Acid Blue 25, Acid Green 41, Acid Blue 45, Mordant Violet 5, Acid Blue 129, Acid Green 25, D&C Green No. 5, Acid Green 27, and combinations thereof.

23 Claims, 2 Drawing Sheets

U.S. PATENT DOCUMENTS

| | | |
|---|---|---|
| 5,009,653 A | 4/1991 | Osborn, III |
| 5,017,227 A | 5/1991 | Koike et al. |
| 5,020,533 A | 6/1991 | Hubbard et al. |
| 5,034,058 A | 7/1991 | Akiyama et al. |
| 5,062,893 A | 11/1991 | Adamic et al. |
| 5,064,694 A | 11/1991 | Gee |
| 5,067,980 A | 11/1991 | Koike et al. |
| 5,069,719 A | 12/1991 | Ono |
| 5,091,004 A | 2/1992 | Tabayashi et al. |
| 5,092,926 A | 3/1992 | Owatari |
| 5,098,474 A | 3/1992 | Pawlowski et al. |
| 5,100,470 A | 3/1992 | Hindagolla et al. |
| 5,100,581 A | 3/1992 | Watanabe et al. |
| 5,108,739 A | 4/1992 | Kurihara et al. |
| 5,122,418 A | 6/1992 | Nakane et al. |
| 5,133,803 A | 7/1992 | Moffatt |
| 5,145,518 A | 9/1992 | Winnik et al. |
| 5,147,343 A | 9/1992 | Kellenberger |
| 5,151,128 A | 9/1992 | Fukushima et al. |
| 5,156,675 A | 10/1992 | Breton et al. |
| 5,160,535 A | 11/1992 | Cooke et al. |
| 5,183,656 A | 2/1993 | Uesaka et al. |
| 5,190,581 A | 3/1993 | Fukushima et al. |
| 5,196,177 A | 3/1993 | Watanabe et al. |
| 5,203,912 A | 4/1993 | Greenwood et al. |
| 5,220,346 A | 6/1993 | Carreira et al. |
| 5,221,332 A | 6/1993 | Kohlmeier |
| 5,223,026 A | 6/1993 | Schwarz, Jr. |
| 5,226,957 A | 7/1993 | Wickramanayake et al. |
| 5,230,732 A | 7/1993 | You et al. |
| 5,230,953 A | 7/1993 | Tsugeno et al. |
| 5,258,065 A | 11/1993 | Fujisawa |
| 5,267,992 A | 12/1993 | Van Tilburg |
| 5,269,840 A | 12/1993 | Morris et al. |
| 5,274,025 A | 12/1993 | Stockle et al. |
| 5,281,662 A * | 1/1994 | Ito et al. .................. 525/54.1 |
| 5,284,703 A | 2/1994 | Everhart et al. |
| 5,302,195 A | 4/1994 | Helbrecht et al. |
| 5,314,855 A | 5/1994 | Thorpe et al. |
| 5,322,061 A | 6/1994 | Brunson |
| 5,340,929 A | 8/1994 | Ono et al. |
| 5,344,872 A | 9/1994 | Debord et al. |
| 5,350,624 A | 9/1994 | Georger et al. |
| 5,354,400 A | 10/1994 | Lavash et al. |
| 5,366,947 A | 11/1994 | Müller et al. |
| 5,370,730 A | 12/1994 | Gregory et al. |
| 5,382,283 A | 1/1995 | Yui et al. |
| 5,382,400 A | 1/1995 | Pike et al. |
| 5,383,450 A | 1/1995 | Hubbard et al. |
| 5,389,094 A | 2/1995 | Lavash et al. |
| 5,407,442 A | 4/1995 | Karapasha |
| 5,407,600 A * | 4/1995 | Ando et al. .................. 516/94 |
| 5,413,568 A | 5/1995 | Roach et al. |
| 5,431,723 A | 7/1995 | Bermes et al. |
| 5,439,514 A | 8/1995 | Kashiwazaki et al. |
| 5,441,561 A | 8/1995 | Chujo et al. |
| 5,462,166 A | 10/1995 | Minton et al. |
| 5,480,636 A | 1/1996 | Maruo et al. |
| 5,484,475 A | 1/1996 | Breton et al. |
| 5,489,283 A | 2/1996 | Van Tilburg |
| 5,512,095 A | 4/1996 | Sens et al. |
| 5,531,817 A | 7/1996 | Shields et al. |
| 5,538,548 A | 7/1996 | Yamazaki |
| 5,540,916 A | 7/1996 | Parks |
| 5,553,608 A | 9/1996 | Reese et al. |
| 5,565,022 A | 10/1996 | Wickramanayake |
| 5,569,231 A | 10/1996 | Emenaker et al. |
| 5,605,566 A | 2/1997 | Yui et al. |
| 5,616,315 A | 4/1997 | Masterman et al. |
| 5,620,430 A | 4/1997 | Bamber |
| 5,626,654 A | 5/1997 | Breton et al. |
| 5,626,655 A | 5/1997 | Pawlowski et al. |
| 5,633,109 A | 5/1997 | Jennings et al. |
| 5,656,072 A | 8/1997 | Kato et al. |
| 5,661,197 A | 8/1997 | Villiger et al. |
| 5,667,572 A | 9/1997 | Taniguch et al. |
| 5,679,138 A | 10/1997 | Bishop et al. |
| 5,679,724 A | 10/1997 | Sacripante et al. |
| 5,681,380 A | 10/1997 | Nohr et al. |
| 5,684,063 A | 11/1997 | Patel et al. |
| 5,693,126 A | 12/1997 | Ito |
| 5,704,930 A | 1/1998 | Lavash et al. |
| 5,725,643 A | 3/1998 | Higashiyama |
| 5,733,272 A | 3/1998 | Brunner et al. |
| 5,749,951 A | 5/1998 | Yoshiike et al. |
| 5,753,026 A | 5/1998 | Kuntz et al. |
| 5,756,561 A | 5/1998 | Wang et al. |
| 5,769,931 A | 6/1998 | Wang et al. |
| 5,777,639 A | 7/1998 | Kageyama et al. |
| 5,785,745 A | 7/1998 | Lauw et al. |
| 5,788,749 A | 8/1998 | Breton et al. |
| 5,788,753 A | 8/1998 | Pawlowski et al. |
| 5,795,985 A | 8/1998 | Hüsler et al. |
| 5,800,654 A | 9/1998 | Davis et al. |
| 5,810,917 A | 9/1998 | Yamazaki et al. |
| 5,813,398 A | 9/1998 | Baird et al. |
| 5,814,685 A | 9/1998 | Satake et al. |
| 5,817,300 A | 10/1998 | Cook et al. |
| 5,833,744 A | 11/1998 | Breton et al. |
| 5,843,509 A | 12/1998 | Calvo Salve et al. |
| 5,852,073 A | 12/1998 | Villiger et al. |
| 5,853,859 A | 12/1998 | Levy et al. |
| 5,855,660 A | 1/1999 | Bujard et al. |
| 5,858,503 A | 1/1999 | Everhart et al. |
| 5,861,144 A | 1/1999 | Peterson et al. |
| 5,868,823 A | 2/1999 | Yamazaki et al. |
| 5,871,872 A | 2/1999 | Matijevic et al. |
| 5,874,067 A | 2/1999 | Lucas et al. |
| 5,879,439 A | 3/1999 | Nagai et al. |
| 5,880,176 A | 3/1999 | Kamoto et al. |
| 5,882,391 A | 3/1999 | Gregory et al. |
| 5,882,392 A | 3/1999 | Gregory et al. |
| 5,882,638 A | 3/1999 | Dodd et al. |
| 5,885,599 A | 3/1999 | Peterson et al. |
| 5,888,286 A | 3/1999 | Gregory et al. |
| 5,891,230 A | 4/1999 | Gregory et al. |
| 5,891,232 A | 4/1999 | Moffatt et al. |
| 5,891,934 A | 4/1999 | Moffatt et al. |
| 5,897,541 A | 4/1999 | Uitenbroek et al. |
| 5,911,816 A | 6/1999 | Gore |
| 5,916,596 A | 6/1999 | Desai et al. |
| 5,928,416 A | 7/1999 | Gundlach et al. |
| 5,928,419 A | 7/1999 | Uemura et al. |
| 5,935,309 A | 8/1999 | Moffatt et al. |
| 5,935,310 A | 8/1999 | Engel et al. |
| 5,942,027 A | 8/1999 | Ikai et al. |
| 5,944,883 A | 8/1999 | Saibara et al. |
| 5,948,155 A | 9/1999 | Yui et al. |
| 5,948,398 A | 9/1999 | Hanamoto et al. |
| 5,955,515 A | 9/1999 | Kimura et al. |
| 5,958,998 A | 9/1999 | Foucher et al. |
| 5,962,566 A | 10/1999 | Grandfils et al. |
| 5,964,926 A | 10/1999 | Cohen |
| 5,964,930 A | 10/1999 | Saibara et al. |
| 5,968,244 A | 10/1999 | Ueda et al. |
| 5,972,389 A | 10/1999 | Shell et al. |
| 5,973,025 A | 10/1999 | Nigam et al. |
| 5,973,027 A | 10/1999 | Howald et al. |
| 5,980,623 A | 11/1999 | Hiraoka et al. |
| 5,981,623 A | 11/1999 | McCain et al. |
| 5,985,229 A | 11/1999 | Yamada et al. |
| 5,993,527 A | 11/1999 | Tochihara et al. |
| 5,993,856 A | 11/1999 | Ragavan et al. |
| 5,998,222 A | 12/1999 | Weimer |
| 6,015,454 A | 1/2000 | Lacroix et al. |
| 6,015,455 A | 1/2000 | Yano et al. |
| 6,019,827 A | 2/2000 | Wickramanayake et al. |
| 6,024,785 A | 2/2000 | Morimoto |
| 6,024,786 A | 2/2000 | Gore |
| 6,025,412 A | 2/2000 | Sacripante et al. |
| 6,033,463 A | 3/2000 | Yui et al. |
| 6,034,154 A | 3/2000 | Kase et al. |
| 6,037,391 A | 3/2000 | Iida |
| 6,045,606 A | 4/2000 | Matzinger |
| 6,048,390 A | 4/2000 | Yano et al. |
| 6,051,057 A | 4/2000 | Yatake et al. |
| 6,090,193 A | 7/2000 | Nigam et al. |

| | | | |
|---|---|---|---|
| 6,096,299 A | 8/2000 | Guarracino et al. | |
| 6,099,627 A | 8/2000 | Saibara et al. | |
| 6,110,266 A | 8/2000 | Gonzalez-Blanco et al. | |
| 6,113,680 A | 9/2000 | Aoyama et al. | |
| 6,121,365 A | 9/2000 | Saibara et al. | |
| 6,129,786 A | 10/2000 | Camara et al. | |
| 6,140,390 A | 10/2000 | Bugner et al. | |
| 6,147,139 A | 11/2000 | Shaw-Klein et al. | |
| 6,149,719 A | 11/2000 | Houle | |
| 6,153,001 A | 11/2000 | Suzucki et al. | |
| 6,156,649 A | 12/2000 | Macholdt et al. | |
| 6,165,440 A | 12/2000 | Esenaliev | |
| 6,171,382 B1 | 1/2001 | Stübbe et al. | |
| 6,200,555 B1 | 3/2001 | Nishijima et al. | |
| 6,210,625 B1 | 4/2001 | Matsushita et al. | |
| 6,225,524 B1 | 5/2001 | Guarracino et al. | |
| 6,277,489 B1 | 8/2001 | Abbott et al. | |
| 6,277,772 B1 | 8/2001 | Gancet et al. | |
| 6,299,867 B1 | 10/2001 | Aoyagi et al. | |
| 6,315,864 B2 | 11/2001 | Anderson et al. | |
| 6,344,218 B1 | 2/2002 | Dodd et al. | |
| 6,358,499 B2 | 3/2002 | Hall-Puzio et al. | |
| 6,358,537 B1 | 3/2002 | Hoshino et al. | |
| 6,361,780 B1 | 3/2002 | Ley et al. | |
| 6,369,290 B1 | 4/2002 | Glaug et al. | |
| 6,376,741 B1 | 4/2002 | Guarracino et al. | |
| 6,387,495 B1 | 5/2002 | Reeves et al. | |
| 6,410,765 B1 | 6/2002 | Wellinghoff et al. | |
| 6,427,693 B1 | 8/2002 | Blackstock et al. | |
| 6,432,872 B1 | 8/2002 | Tsushio et al. | |
| 6,479,150 B1 | 11/2002 | Liu et al. | |
| 6,486,227 B2 | 11/2002 | Nohr et al. | |
| 6,638,918 B2 | 10/2003 | Davison et al. | |
| 6,639,004 B2 | 10/2003 | Falat et al. | |
| 6,645,569 B2 * | 11/2003 | Cramer et al. | 427/466 |
| 6,680,279 B2 | 1/2004 | Cai et al. | |
| 6,680,289 B1 | 1/2004 | Woo et al. | |
| 6,703,451 B2 * | 3/2004 | Hosokawa et al. | 525/340 |
| 6,780,896 B2 | 8/2004 | MacDonald et al. | |
| 7,008,979 B2 | 3/2006 | Schottman et al. | |
| 2001/0023338 A1 | 9/2001 | Guarracino et al. | |
| 2002/0106466 A1 | 8/2002 | Hausmann et al. | |
| 2002/0142937 A1 | 10/2002 | Carter et al. | |
| 2002/0149656 A1 | 10/2002 | Nohr et al. | |
| 2002/0177621 A1 | 11/2002 | Hanada et al. | |
| 2003/0082237 A1 | 5/2003 | Cha et al. | |
| 2003/0099718 A1 | 5/2003 | Burrell et al. | |
| 2003/0181540 A1 | 9/2003 | Quellet et al. | |
| 2003/0203009 A1 * | 10/2003 | MacDonald | 424/443 |
| 2004/0116882 A1 * | 6/2004 | Erspamer et al. | 604/359 |
| 2004/0120904 A1 | 6/2004 | Lye et al. | |
| 2004/0120921 A1 | 6/2004 | Quincy, III et al. | |
| 2004/0122387 A1 | 6/2004 | Long et al. | |
| 2004/0176736 A1 | 9/2004 | Christon et al. | |

FOREIGN PATENT DOCUMENTS

| | | |
|---|---|---|
| EP | 0376448 B1 | 7/1990 |
| EP | 0389015 A2 | 9/1990 |
| EP | 0389015 A3 | 9/1990 |
| EP | 0389023 A2 | 9/1990 |
| EP | 0389023 A3 | 9/1990 |
| EP | 0483500 A1 | 5/1992 |
| EP | 0510619 A1 | 10/1992 |
| EP | 0251783 B1 | 4/1993 |
| EP | 0749295 B1 | 12/1996 |
| EP | 0972563 A1 | 1/2000 |
| EP | 1034800 A1 | 9/2000 |
| EP | 1157672 A1 | 11/2001 |
| EP | 1214878 A1 | 6/2002 |
| EP | 1216675 A1 | 6/2002 |
| EP | 1315526 B1 | 11/2004 |
| GB | 2257428 A | 1/1993 |
| JP | 62149322 | 7/1987 |
| JP | 10323700 A * | 12/1998 |
| WO | WO 9111977 A1 | 8/1991 |
| WO | WO 9112029 A1 | 8/1991 |
| WO | WO 9112030 A1 | 8/1991 |
| WO | WO 9725076 A1 | 7/1997 |
| WO | WO 9814524 A1 | 4/1998 |
| WO | WO 9820915 A1 | 5/1998 |
| WO | WO 9826808 A2 | 5/1998 |
| WO | WO 9826808 A3 | 5/1998 |
| WO | WO 9826808 A2 * | 6/1998 |
| WO | WO 9947252 A2 | 3/1999 |
| WO | WO 9947253 A1 | 3/1999 |
| WO | WO 9947252 A3 | 9/1999 |
| WO | WO 0003797 A1 | 1/2000 |
| WO | WO 0059555 A1 | 10/2000 |
| WO | WO 0066090 A1 | 12/2000 |
| WO | WO 0076558 A1 | 12/2000 |
| WO | WO 0106054 A1 | 1/2001 |
| WO | WO 0202347 A1 | 1/2002 |
| WO | WO 0226272 A1 | 4/2002 |
| WO | WO 0249559 A2 | 6/2002 |
| WO | WO 02055115 A1 | 7/2002 |
| WO | WO 02083297 A1 | 10/2002 |
| WO | WO 02094329 A1 | 11/2002 |
| WO | WO 02095112 A1 | 11/2002 |
| WO | WO 03025067 A1 | 3/2003 |
| WO | WO 03032959 A1 | 4/2003 |
| WO | WO 03051278 A2 | 6/2003 |
| WO | WO 03051278 A3 | 6/2003 |
| WO | WO 03088931 A2 | 10/2003 |
| WO | WO 03092885 A1 | 11/2003 |
| WO | WO2004/060378 A2 | 7/2004 |

OTHER PUBLICATIONS

Abstract of Japanese Patent No. JP1262868, Oct. 19, 1989.
Abstract of Japanese Patent JP2000129179, May 9, 2000.
Abstract of Japanese Patent No. JP2157039, Jun. 15, 1990.
Abstract of Japanese Patent No. JP3195562, Aug. 27, 1991.
Abstract of Japanese Patent No. JP4335141, Nov. 24, 1992.
Abstract of Japanese Patent No. JP5106199, Apr. 27, 1993.
Abstract of Japanese Patent No. JP56143272, Nov. 7, 1981.
Abstract of Japanese Patent No. JP6285140, Oct. 11, 1994.
Abstract of Japanese Patent No. JP63072337 Apr. 2, 1988.
Abstract of Japanese Patent No. JP63105078, May 10, 1988.
Abstract of Japanese Patent No. JP8152409, Jun. 11, 1996.
Abstract of Japanese Patent No. JP8259868, Oct. 8, 1996.
Abstracts of Papers, 221$^{st}$ ACS National Meeting, San Diego, CA, Apr. 1-5, 2000.
Article—*Adsorption and Encapsulation of Fluorescent Probes in Nanoparticles*, Olga V. Makarova, Agnes E. Ostafin, Hirokazu Miyoshi, and James R. Norris, Jr., The Journal of Physical Chemistry B®, vol. 103, No. 43, Oct. 28, 1999, pp. 9080-9084.
Article—*Adsorption of Dyes on Nanosize Modified Silica Particles*, Guangwei Wu, Athanasia Koliadima, Yie-Shein Her, and Egon Matijevic, Journal of Colloid and Interface Sciences, vol. 195, 1997, pp. 222-228.
Article—*Adsorption of Gases in Multimolecular Layers*, Stephen Brunauer, P. H. Emmett, and Edward Teller, American Chemical Society, vol. 60, Jan.-Jun. 1938, pp. 309-319.
Article—*Adsorption of Proteins and Antibiotics on Porous Alumina Membranes*, Yi Hua Ma, Aseem Bansal, and William M. Clark, Fundamentals of Adsorption, vol. 80, 1992, pp. 389-396.
Article—*Development of Novel Dye-Doped Silica Nanoparticles for Biomarker Application*, Swadeshmukul Santra, Kemin Wang, Rovelyn Tapec, and Weihong Tan, Journal of Biomedical Optics, vol. 6, No. 2, Apr. 2001, pp. 160-166.
Article—*Industrial Organic Pigments*, W. Herbst and K. Hunger, 1997, 6 pages.
Article—*Nanoparticles based on polyelectrolyte complexes: effect of structure and net charge on the sorption capability for solved organic molecules*, H.-M. Buchhammer, G. Petzold, and K. Lunkwitz, Colloid Polym. Sci., vol. 278, 2000, pp. 841-847.
Article—*Purification and Characterization of Urease from Helicobacter pylori*, Bruce E. Dunn, Gail P. Campbell, Guillermo I. Perez-Perez, and Martin J. Blaser, The Journal of Biological Chemistry, vol. 265, No. 16, Jun. 5, 1990, pp. 9464-1990.
Article—*Silent Discharges for the Generation of Ultraviolet and Vacuum Ultraviolet Excimer Radiation*, Ulrich Kogelschatz, Pure and Applied Chemistry, vol. 62, No. 9, 1990, pp. 1667-1674.
Article—*Study of the urea thermal decomposition (pyrolysis) reaction and importance to cyanuric acid production*, Peter M. Schaber, James Colson, Steven Higgins, Ed Dietz, Daniel Thielen, Bill Anspach, and Jonathan Brauer, American Laboratory, Aug. 1999, pp. 13-21.
Article—*UV Excimer Radiation from Dielectric-Barrier Discharges*, B. Eliasson and U. Kogelschatz, Applied Physics B, vol. B 46, No. 4, Aug. 1988, pp. 299-303.
Paper—*Uniform Deposition of Ultrathin Polymer Films on the Surfaces of $Al_2O_3$ Nanoparticles by a Plasma Treatment*, Donglu Shi, S. X. Wang, Wim J. van Ooij, L. M. Wang, Jiangang Mao, and Zhou Yu, University of Cincinnati and University of Michigan, Jun. 2000, pp. 1-15.
Product Information—Aldrich, 2000-2001, 4 pages.
Product Information Sheets on Snowtex®, 6 pages, 2005.
MacDonald, et al., U.S. Appl. No. 10/686,933, filed Oct. 16, 2003, Method for Reducing Odor Using Colloidal Nanoparticles.
McGrath, et al., U.S. Appl. No. 10/686,939, filed Oct. 16, 2003, Method for Reducing Odor Using Metal-Modified Particles.
Wu, et al., U.S. Appl. No. 10/686,937, filed Oct. 16, 2003, Method for Reducing Odor Using Coordinated Polydentate Compounds.
Do, et al., U.S. Appl. No. 10/686,938, filed Oct. 16, 2003, Method for Reducing Odor Using Metal-Modified Silica Particles.
Fish, et al., U.S. Appl. No. 10/687,425, filed Oct. 16, 2003, Odor Absorbing Extrudates.
MacDonald, et al., U.S. Appl. No. 10/687,270, filed Oct. 16, 2003, Visual Indicating Device for Bad Breath.
MacDonald, et al., U.S. Appl. No. 10/686,687, filed Oct. 16, 2003, Durable Charged Particle Coatings and Materials.
MacDonald, et al., U.S. Appl. No. 10/687,269, filed Oct. 16, 2003, Odor Controlling Article Including a Visual Indicating Device for Monitoring Odor Absorption.
Boga, et al., U.S. Appl. No. 10/687,327, filed Oct. 16, 2003, Method and Device for Detecting Ammonia Odors and *Helicobacter pylori* Urease Infection.
Urlaub, et al., U.S. Appl. No. 10/687,004, filed Oct. 16, 2003, High Surface Area Material Blends for Odor Reduction, Articles Utilizing Such Blends and Methods of Using Same.
MacDonald, et al., U.S. Appl. No. 10/731,257, filed Dec. 9, 2003, Triggerable Delivery System for Pharmaceutical and Nutritional Compounds and Methods of Utilizing Same.
Quincy, III et al., U.S. Appl. No. 10/723,761, filed Nov. 26, 2003, Odor Control in Personal Care Products.

* cited by examiner

ODOR-REDUCING QUINONE COMPOUNDS

RELATED APPLICATIONS

The present application is a continuation-in-part of U.S. application Ser. No. 10/325,474, which was filed on Dec. 20, 2002.

BACKGROUND OF THE INVENTION

Odor control additives have been conventionally incorporated into substrates for a variety of reasons. For instance, U.S. Pat. No. 6,225,524 to Guarracino, et al. describes a substrate having an odor control composition that includes an absorbent gelling material and silica. Likewise, U.S. Pat. No. 6,376,741 to Guarracino, et al. describes a substrate having an odor control composition that includes silica and a zeolite (i.e., crystalline aluminosilicate). For instance, one type of silica said to be preferred in Guarracino, et al. ('524 patent) is amorphous silica having a particle size of 4-12 microns and a pore volume of 1-2 g/ml. Another type of preferred silica is said to be a silica gel having a medium pore diameter of from 90 to 110 angstroms, a surface area of from 250 $m^2/g$ to 350 $m^2/g$, and an average particle size of from 63 to 200 microns. Unfortunately, conventional odor control compositions, such as described above, have proven ineffective in obtaining the full level of odor control desired in many applications.

As such, a need exists for an odor control composition that may exhibit improved odor control properties, particularly when applied to a substrate.

SUMMARY OF THE INVENTION

In accordance with one embodiment of the present invention, an article of manufacture is disclosed that comprises a fibrous substrate. The fibrous substrate contains an odor control composition, which is comprised of an odor-reducing quinone compound and high-surface area particles (e.g., colloidal nanoparticles). For example, the odor-reducing quinone compound may be an anthraquinone having the following structure:

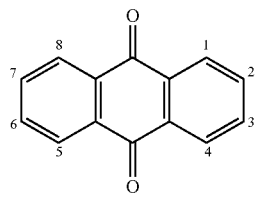 [SMILES: O=C1c2ccccc2C(=O)c2ccccc21]

wherein the numbers 1 through 8 refer to optional substitution positions for functional groups. In one embodiment, for example, positions 5 through 8 of the anthraquinone are unsubstituted with functional groups. Examples of such quinone compounds may include those obtained from a dye selected from the group consisting of Acid Blue 25, Acid Green 41, Acid Blue 45, Mordant Violet 5, Acid Blue 129, Acid Green 25, D&C Green No. 5, Acid Green 27, and combinations thereof.

In accordance with another embodiment of the present invention, an absorbent article is disclosed that comprises at least one liquid transmissive layer and a liquid absorbent core. The liquid-transmissive layer, liquid-absorbent core, or combinations thereof, contain an odor control composition. The odor control composition comprises an odor-reducing quinone compound. In accordance with still another embodiment of the present invention, an odor control composition is disclosed that comprises an odor-reducing quinone compound and high surface area particles. Further, in accordance with yet another embodiment of the present invention, a method for reducing odor is disclosed that comprises selecting from the group consisting of quinone dyes a quinone compound that is capable of reducing odor; forming an odor control composition that comprises the quinone compound; and contacting the odor control composition with an odorous compound.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figure in which.

Figure 1:
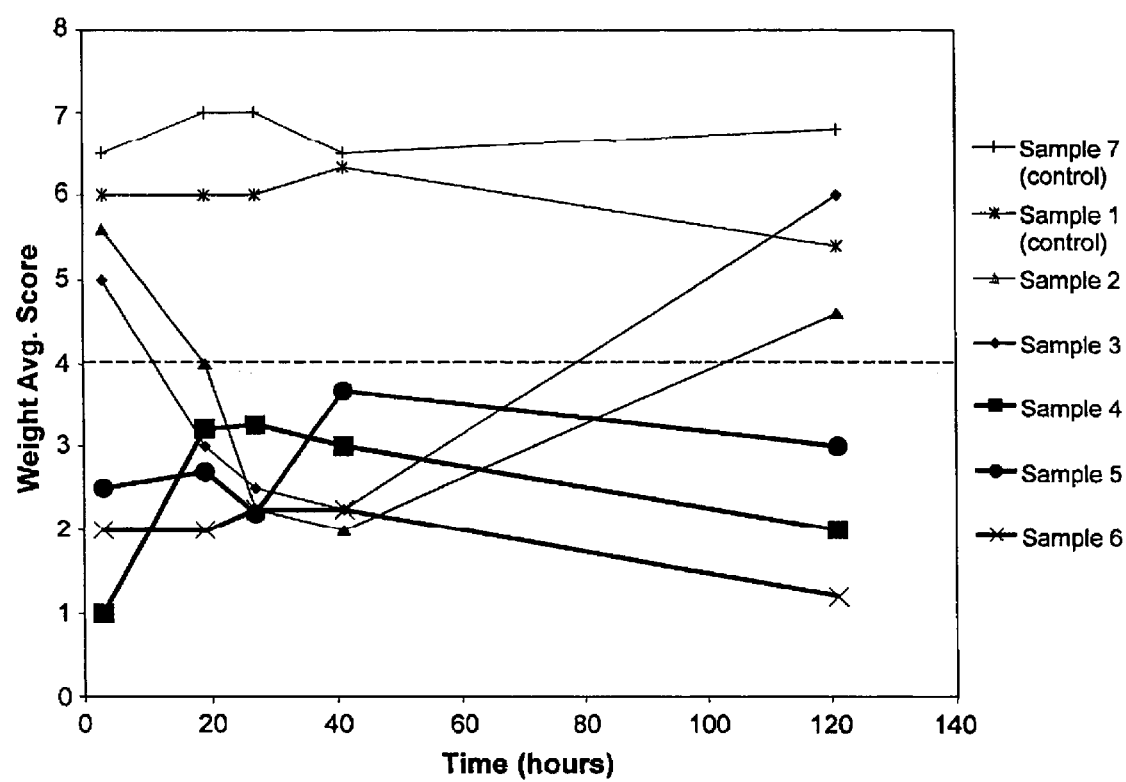
FIG. 1 is a graphical depiction of the results of Example 2, in which the average garlic odor control ranking is plotted versus time (hours)

Repeat use of reference characters in the present specification and drawings is intended to represent same or analogous features or elements of the invention.

Other features and aspects of the present invention are discussed in greater detail below.

DETAILED DESCRIPTION OF REPRESENTATIVE EMBODIMENTS

Definitions

As used herein, the term "zeta potential" refers to the potential gradient that arises across an interface. Zeta potential measurements may be taken using, for instance, a Zetapals instrument available from the Brookhaven Instrument Corporation of Holtsville, N.Y. For example, zeta potential measurements may be conducted by adding one to three drops of a sample into a cuvet containing 1 millimolar KCl solution, using the instrument's default functions preset for aqueous solutions.

As used herein, an "absorbent article" refers to any article capable of absorbing water or other fluids. Examples of some absorbent articles include, but are not limited to, personal care absorbent articles, such as diapers, training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; textile fabrics; clothing articles; and so forth. Materials and processes suitable for forming such absorbent articles are well known to those skilled in the art.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc.

As used herein, the term "meltblowing" refers to a process in which fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonding" refers to a process in which small diameter substantially continuous fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. Nos. 4,340,563 to Appel, et al., 3,692,618 to Dorschner, et al., 3,802,817 to Matsuki, et al., 3,338,992 to Kinney, 3,341,394 to Kinney, 3,502,763 to Hartman, 3,502,538 to Levy, 3,542,615 to Dobo, et al., and 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to an odor control composition that includes a quinone compound. Quinones refer to a class of compounds that possess a quinoid ring, such as anthraquinones, naphthaquinones, benzoquinones, hydroquinones, and so forth. Anthraquinones, for instance, have the following general formula:

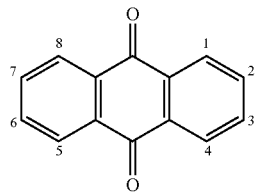

The numbers shown in the general formula represent a location on the fused ring structure at which substitution of a functional group may occur. Some examples of such functional groups that may be substituted on the fused ring structure include halogen groups (e.g., chlorine or bromine groups), sulfonyl groups (e.g., sulfonic acid salts), alkyl groups, benzyl groups, amino groups (e.g., primary, secondary, tertiary, or quaternary amines), carboxy groups, cyano groups, hydroxy groups, phosphorous groups, etc. Functional groups that result in an ionizing capability are often referred to as "chromophores." Substitution of the ring structure with a chromophore causes a shift in the absorbance wavelength of the compound. Thus, depending on the type of chromophore (e.g., hydroxyl, carboxyl, amino, etc.) and the extent of substitution, a wide variety of quinones may be formed with varying colors and intensities. Other functional groups, such as sulfonic acids, may also be used to render certain types of compounds (e.g., higher molecular weight anthraquinones) water-soluble.

Anthraquinone compounds may be classified for identification by their Color Index (Cl) number, which is sometimes called a "standard." For instance, some suitable anthraquinones that may be used in the present invention, as classified by their "Cl" number, include Acid Black 48, Acid Blue 25 (D&C Green No. 5), Acid Blue 40, Acid Blue 41, Acid Blue 45, Acid Blue 129, Acid Green 25, Acid Green 27, Acid Green 41, Mordant Red 11 (Alizarin), Mordant Black 13 (Alizarin Blue Black B), Mordant Red 3 (Alizarin Red S), Mordant Violet 5 (Alizarin Violet 3R), Natural Red 4 (Carminic Acid), Disperse Blue 1, Disperse Blue 3, Disperse Blue 14, Natural Red 16 (Purpurin), Natural Red 8, Reactive Blue 2, and so forth. For instance, the structures of Acid Blue 25, Acid Green 41, Acid Blue 45, Mordant Violet 5, Acid Blue 129, Acid Green 25, and Acid Green 27 are set forth below:

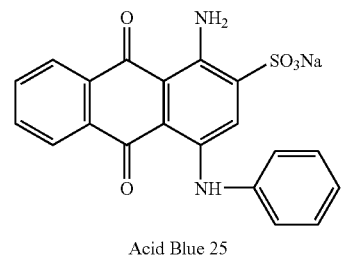

Acid Blue 25

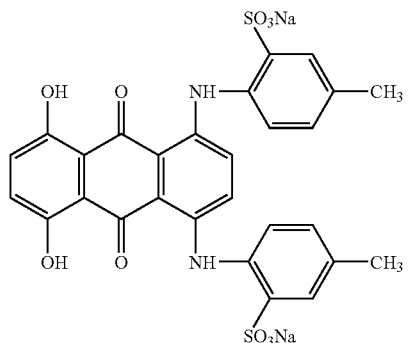

Acid Green 41

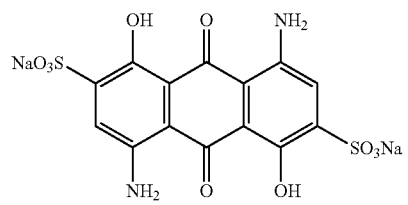

Acid Blue 45

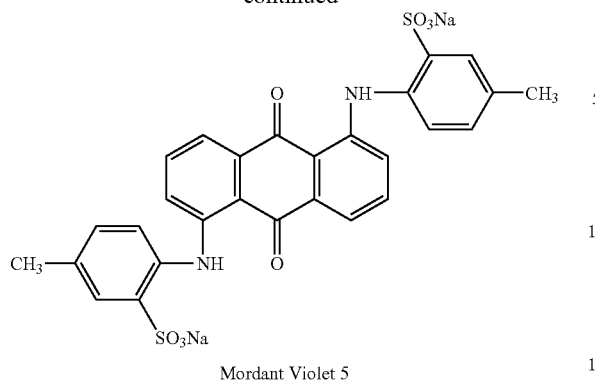

Mordant Violet 5

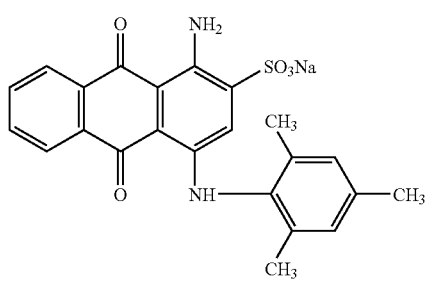

Acid Blue 129

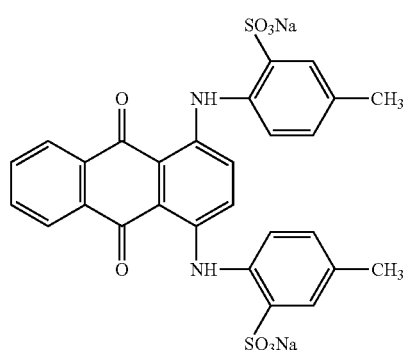

Acid Green 25

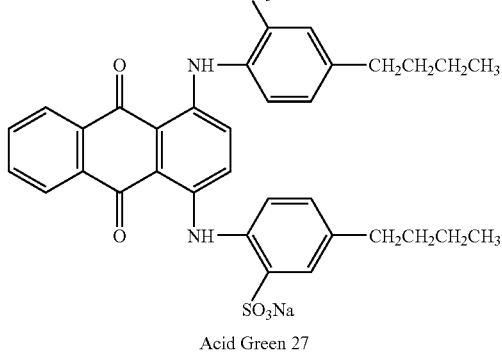

Acid Green 27

As stated above, other quinones may also be used in the present invention. For example, naphthaquinones may be used that have the following general formula:

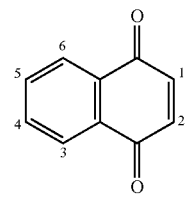

The locations 1-6 of the naphthaquinone compounds may be substituted with functional groups in the manner described above. For instance, suitable examples of naphthaquinone compounds that may be used in the present invention include 1,4 naphthaquinone and 1,2 naphthaquinone, which have the following structures:

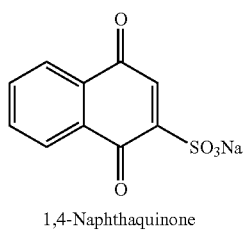

1,4-Naphthaquinone

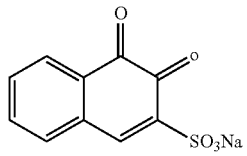

1,2-Naphthaquinone

Besides their well-known ability to impart color, the present inventors have unexpectedly discovered that certain quinone compounds may also eliminate odor. Without intending to be limited by theory, it is believed that the odor caused by many compounds is eliminated by the transfer of electrons to and/or from the odorous compound. Specifically, electron reduction of odorous compounds via a reduction/oxidation ("redox") reaction is believed to inhibit the production of the characteristic odor associated therewith. The surprising discovery that certain quinone compounds are able to eliminate odor is believed to be due their ability to function as an oxidizing agent in a redox reaction. Many common odorous compounds are capable of oxidizing (i.e., donate electrons) via a redox reaction. For instance, odorous compounds may include mercaptans (e.g., ethyl mercaptan), ammonia, amines (e.g., trimethylamine (TMA), triethylamine (TEA), etc.), sulfides (e.g., hydrogen sulfide, dimethyl disulfide (DMDS), etc.), ketones (e.g., 2-butanone, 2-pentanone, 4-heptanone, etc.) carboxylic acids (e.g., isovaleric acid, acetic acid, propionic acid, etc.), aldehydes, terpenoids, hexanol, heptanal, pyridine, and so forth. Upon oxidation, the odors associated with such compounds are often eliminated or at least lessened. It is also believed that the reduction of the quinone compound via the redox reaction is readily reversible, and thus the reduced quinone compound may be re-oxidized by any known oxidizing agent (e.g., oxygen, air, etc.). The reduction/oxidation reactions are rapid and may take place at room temperature. Thus, although the odor control mechanism may consume the quinone compounds, they may simply be regenerated by exposure to air. Thus, long-term odor control may be achieved without significantly affecting the ability of the quinone compound to impart the desired color.

The ability of quinone compounds to accept electrons from another substance (i.e., be reduced) may be quantified using a technique known as redox potentiometry. Redox potentiometry is a technique that measures (in volts) the affinity of a substance for electrons—its electronegativity—compared with hydrogen (which is set at 0). Substances more strongly electronegative than (i.e., capable of oxidizing) hydrogen have positive redox potentials. Substances less electronegative than (i.e., capable of reducing) hydrogen have negative redox potentials. The greater the difference between the redox potentials of two substances ($\Delta E$), the greater the vigor with which electrons will flow spontaneously from the less positive to the more positive (more electronegative) substance. As is well known in the art, redox potential may be measured using any of a variety of commercially available meters, such as an Oxidation Reduction Potential (ORP) tester commercially available from Hanna Instruments, Inc. of Woonsocket, R.I. The redox potential of the quinone compounds may, for instance, be less than about −50 millivolts (mV), in some embodiments less than about −150 mV, in some embodiments less than about −300 mV, and in some embodiments, less than about −500 mV. Although not always the case, the redox potential may vary based on the number and location of functional groups, such as sulfonic acid, on the quinone structure. For example, 2-sulfonic acid anthraquinone has a redox potential of −380 mV; 2,6-disulfonic acid anthraquinone has a redox potential of −325 mV; and 2,7-disulfonic acid anthraquinone has a redox potential of −313 mV. Likewise, 2-sulfonic acid naphthaquinone has a redox potential of −60 mV. The use of other functional groups may also have an affect on the ultimate redox potential of the compound. For example, Acid Blue 25, which also contains amino- and aramid functional groups, has a redox potential of −605 mV.

In addition to their ability to oxidize odorous compounds, the present inventors have also discovered that the chemical structure of certain quinone compounds results in improved odor elimination. For example, anthraquinone compounds that have at least one unsubstituted ring may result in better odor inhibition than those that are substituted at each ring with a functional group. Interestingly, anthraquinone compounds that are unsubstituted at the "first" ring (i.e., positions 5 through 8) appear to be particularly effective in reducing odor. Suitable examples of anthraquinone compounds that are unsubstituted at locations 5 through 8 include, but are not limited to, Acid Blue 25, Acid Blue 129, Acid Green 25, and Acid Green 27, the structures of which are set forth above.

Although the quinone compounds of the present invention are capable of achieving high levels of odor reduction, it is sometimes desired to further enhance the level of odor reduction through the use of high-surface area particles that act as a carrier for the compound. In some cases, the quinone compound is believed to form a coordinate bond with an atom of the particles (e.g., aluminum) via oxygen atoms present in the quinone structure. As used herein, a "coordinate bond" refers to a shared pair of electrons between two atoms, wherein one atom supplies both electrons to the pair. When utilized, the high surface area of such particles may provide a further method of reducing odor.

The high-surface area particles may be formed from a variety of materials, including, but not limited to, silica, alumina, zirconia, magnesium oxide, titanium dioxide, iron oxide, zinc oxide, copper oxide, organic compounds such as polystyrene, and combinations thereof. The particles may have a surface area of from about 50 square meters per gram ($m^2/g$) to about 1000 $m^2/g$, in some embodiments from about 100 $m^2/g$ to about 600 $m^2/g$, and in some embodiments, from about 180 $m^2/g$ to about 240 $m^2/g$. Surface area may be determined by the physical gas adsorption (B.E.T.) method of Bruanauer, Emmet, and Teller, Journal of American Chemical Society, Vol. 60, 1938, p. 309, with nitrogen as the adsorption gas.

The particles may possess various forms, shapes, and sizes depending upon the desired result. For instance, the particles may be in the shape of a sphere, crystal, rod, disk, tube, string, etc. The average size of the particles is generally less than about 500 microns, in some embodiments less than about 100 microns, in some embodiments less than about 100 nanometers, in some embodiments from about 1 to about 50 nanometers, in some embodiments from about 2 to about 50 nanometers, and in some embodiments, from about 4 to about 20 nanometers. As used herein, the average size of a particle refers to its average length, width, height, and/or diameter. If desired, the particles may also be relatively nonporous or solid. That is, the particles may have a pore volume that is less than about 0.5 milliliters per gram (ml/g), in some embodiments less than about 0.4 milliliters per gram, in some embodiments less than about 0.3 ml/g, and in some embodiments, from about 0.2 ml/g to about 0.3 ml/g. Without intending to be limited by theory, it is believed that particles having such a small size and high surface area may improve the adsorption capability for many odorous compounds. Moreover, it is believed that the solid nature, i.e., low pore volume, of the particles may enhance the uniformity and stability of the particles, without sacrificing their odor adsorption characteristics.

Regardless of the material used to form the high-surface area particles, the particles may be selected to possess a "zeta potential" that is opposite to a substrate to which it is applied. Although not required, the use of particles having an opposite zeta potential to the substrate may facilitate the binding of the particles thereto through ionic interaction. For example, in some embodiments of the present invention, the particles may have a positive zeta potential of greater than about +20 millivolts (mV), in some embodiments greater than about +30 mV, and in some embodiments, greater than about +40 mV. By possessing a positive surface charge, the particles are well suited for binding to a substrate that carries a negative surface charge (e.g., substrate containing cellulosic fibers) through ionic attraction. Depending upon the difference in charge between the particles and the substrate, the bond may sometimes be relatively permanent and substantive. Consequently, chemical binders or other attachment mechanisms may not be required. In some cases, the charge of the particles may also allow bonding to occur with the quinone dye through ionic attraction. For example, positively-charged particles may bond to some extent to negatively-charged quinone compounds (e.g., acid dyes).

A positive zeta potential may be imparted to the high-surface area particles of the present invention in a variety of different ways. In one embodiment, the particles are formed entirely from a positively charged material. For example, alumina particles may be used for odor reduction in accordance with the present invention. Some suitable alumina particles are described in U.S. Pat. No. 5,407,600 to Ando, et al., which is incorporated herein in its entirety by reference thereto for all purposes. Further, examples of commercially available alumina particles include, for instance, Aluminasol 100, Aluminasol 200, and Aluminasol 520, which are available from Nissan Chemical Industries Ltd. Alternatively, the positive zeta potential may be imparted by a continuous or discontinuous coating present on the surface of a core material. In some instances, these particles may actually possess a better stability over various pH ranges than particles formed entirely from positively charged materials. In one particular embodiment, for example, the particles are formed from silica particles coated with alumina. A commercially available example of such alumina-coated silica particles is Snowtex-AK, which is available from Nissan Chemical of Houston, Tex.

Silica particles possess units that may or may not be joined together. Whether or not such units are joined generally depends on the conditions of polymerization. For instance, the acidification of a silicate solution may yield $Si(OH)_4$. If the pH of this solution is reduced below 7 or if a salt is added, then the units may tend to fuse together in chains and form a "gel." On the other hand, if the pH is kept at a neutral pH or above 7, the units may tend to separate and gradually grow to form a "sol." Silica particles may generally be formed according to any of a variety of techniques well known in the art, such as dialysis, electrodialysis, peptization, acid neutralization, and ion exchange. Some examples of such techniques are described, for instance, in U.S. Pat. Nos. 5,100,581 to Watanabe, et al.; 5,196,177 to Watanabe, et al.; 5,230,953 to Tsugeno, et al. and 5,985,229 to Yamada, et al., which are incorporated herein in their entirety by reference thereto for all purposes.

For exemplary purposes only, one embodiment of an ion-exchange technique for forming an alumina-coated silica sol will now be described in more detail. Initially, an alkali metal silicate is provided that has a molar ratio of silicon ($SiO_2$) to alkali metals ($M_2O$) of from about 0.5 to about 4.5. For instance, sodium water glass may be utilized that has a molar ratio of from about 2 to about 4. An aqueous solution of the alkali metal silicate is obtained by dissolving it in water at a concentration of, for instance, from about 2 wt. % to about 6 wt. %. The alkali metal silicate-containing aqueous solution may then be contacted with one or more ion-exchange resins. For instance, the solution may first be contacted with a strong-acid to ion-exchange all the metal ions in the aqueous solution. Examples of such strong acids include, but are not limited to, hydrochloric acid, nitric acid, sulfuric acid, and so forth. The contact may be accomplished by passing the aqueous solution through a column filled with the strong acid at a temperature of from about 0° C. to about 60° C., and in some embodiments, from about 5° C. to about 50° C. After passing through the column, the resulting silicic acid-containing aqueous solution may have a pH value of from about 2 to about 4. If desired, another strong acid may be added to the silicic acid-containing aqueous solution to convert the impurity metal components into dissociated ions. This additional strong acid may decrease the pH value of the resulting solution to less than about 2, and in some embodiments, from about 0.5 to about 1.8.

The metal ions and the anions from the strong acid may be removed from the solution by consecutive application of a strong acid (i.e., cation-exchange resin) and strong base (anion-exchange resin). Examples of suitable strong bases include, but are not limited to, sodium hydroxide, potassium hydroxide, and so forth. As a result of this consecutive application, the silicic acid-containing aqueous solution may have a pH value of from about 2 to about 5. This acidic aqueous solution may then be contacted with one or more additional strong bases to stabilize the solution at a pH value of from about 7 to about 9.

The stabilized silicic acid-containing aqueous solution is then fed to a container in which the liquid temperature is maintained at from about 70° C. to about 100° C. This process results in an increase in concentration of the silica to from about 30 wt. % to about 50 wt. %. The stable aqueous silica sol may then be consecutively contacted with a strong acid and strong base, such as described above, so that the resulting aqueous silica sol is substantially free from polyvalent metal oxides, other than silica. Finally, ammonia may be added to the aqueous sol to further increase its pH value to from about 8 to about 10.5, thereby forming a stable aqueous silica sol having a silica concentration of from about 30 wt. % to about 50 wt. %, a mean particle size of from about 10 to about 30 nanometers, and that is substantially free from any polyvalent metal oxides, other than silica.

To coat the silica sol with alumina, it is mixed with an aqueous solution of from about 0.2 wt. % to about 10 wt. % of a basic metal salt based on the amount of $SiO_2$ in the silica sol. Examples of some suitable basic metal salts that may be used include, but are not limited to, aluminum chloride, aluminum acetate, aluminum nitrate, aluminum formate, and so forth. The resulting aqueous sol contains colloidal silica particles coated with ions of aluminum. In some instances, other materials may be coated onto the silica instead of, or in conjunction with, the alumina. For example, zirconia may be coated onto the silica sol by using a zirconium-based salt.

The aqueous sol is then adjusted to pH of from about 4 to about 7 with an alkaline aqueous solution to give a positively charged silica sol. The alkaline aqueous solution may include, for instance, alkali metal hydroxides (such as lithium, sodium, potassium, rubidium, and cesium hydroxides), ammonium hydroxide, water-soluble quaternary ammonium hydroxides, guanidine hydroxide, water-soluble alkylamines (such as ethylamine, isopropylamine, and n-propylamine), water-soluble alkanolamines (such as monoethanolamine and triethanolamine), benzylamine, and piperidine. The alkaline substance may be present in the solution at a concentration of from about 0.5 wt. % to about 30 wt %. If desired, the resulting alkaline particles may be subjected to one or more additional consecutive applications of negatively charged silica particles and a basic metal salt to form a more stable positively charged silica sol having the desired particle size.

When utilized, the amount of high-surface area particles may generally vary in relation to the quinone compound. For example, the ratio of the high-surface area particles to the quinone compound may be from about 10 to about 10,000, in some embodiments from about 50 to about 5,000, and in some embodiments, from about 100 to about 1,000.

If desired, the odor control composition may be applied to a substrate. For example, the quinone compound and/or high-surface area particles may be mixed together to form the odor control composition prior to application to the substrate. Alternatively, components of the odor control composition may be applied separately to the substrate (e.g., high-surface area particles are applied prior to the quinone compound). Regardless, the substrate may provide an increased surface area to facilitate the adsorption of odorous compounds. In addition, the substrate may also serve other purposes, such as water absorption. Besides reducing odor in accordance with the present invention, the quinone compounds may also impart an aesthetic design or pattern to the substrate as is well known in the art. Thus, by carefully selecting the particular type of quinone compound utilized, the resulting substrate may achieve improved odor reduction and also possess a desired color and/or pattern. This may result in significant cost savings and efficiency in that dyes and odor reducing agents (e.g., activated carbon) are usually considered separate treatments.

Any of a variety of different substrates may be incorporated with the odor control composition in accordance with the present invention. For instance, nonwoven fabrics, woven fabrics, knit fabrics, wet-strength paper, film, foams, etc., may be applied with the odor control composition. When utilized, the nonwoven fabrics may include, but are not limited to, spunbonded webs (apertured or non-apertured), meltblown webs, bonded carded webs, air-laid webs, coform webs, hydraulically entangled webs, and so forth. In some embodiments, for example, the odor control composition may be utilized in a paper product containing one or more paper webs, such as facial tissue, bath tissue, paper towels, napkins, and so forth. The paper product may be single-ply in which the web forming the product includes a single layer or is stratified (i.e., has multiple layers), or multi-ply, in which the webs forming the product may themselves be either single or multi-layered. Normally, the basis weight of such a paper product is less than about 120 grams per square meter (gsm), in some embodiments less than about 80 gsm, in some embodiments less than about 60 grams per square meter, and in some embodiments, from about 10 to about 60 gsm.

Any of a variety of materials can also be used to form the paper web(s) of the product. For example, the material used to make the paper product may include fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Kimberly-Clark Corporation under the trade designations "Longlac-19". Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, and so forth. In addition, in some instances, synthetic fibers can also be utilized. Some suitable synthetic fibers can include, but are not limited to, rayon fibers, ethylene vinyl alcohol copolymer fibers, polyolefin fibers, polyesters, and so forth.

If desired, the substrate may form all or a portion of an absorbent article. In one embodiment, for instance, the absorbent article includes a liquid-transmissive bodyside liner, a liquid-transmissive surge layer below the bodyside liner, a liquid-absorbent core below the surge layer, and a moisture vapor permeable, liquid impermeable outer cover below the absorbent core. A substrate treated with the odor control composition of the present invention may be employed as any one or more of the liquid transmissive (non-retentive) and absorbent layers. An absorbent core of the absorbent article, for instance, may be formed from an absorbent nonwoven web that includes a matrix of hydrophilic fibers. In one embodiment, the absorbent web may contain a matrix of cellulosic fluff fibers. One type of fluff that may be used in the present invention is identified with the trade designation CR1654, available from U.S. Alliance, Childersburg, Ala., U.S.A., and is a bleached, highly absorbent sulfate wood pulp containing primarily soft wood fibers. In another embodiment, the absorbent nonwoven web may contain a hydroentangled web. Hydroentangling processes and hydroentangled composite webs containing various combinations of different fibers are known in the art. A typical hydroentangling process utilizes high pressure jet streams of water to entangle fibers and/or filaments to form a highly entangled consolidated fibrous structure, e.g., a nonwoven fabric. Hydroentangled nonwoven fabrics of staple length fibers and continuous filaments are disclosed, for example, in U.S. Pat. Nos. 3,494,821 to Evans and 4,144,370 to Boulton, which are incorporated herein in their entirety by reference thereto for all purposes. Hydroentangled composite nonwoven fabrics of a continuous filament nonwoven web and a pulp layer are disclosed, for example, in U.S. Pat. Nos. 5,284,703 to Everhart, et al. and 6,315,864 to Anderson, et al., which are incorporated herein in their entirety by reference thereto for all purposes.

Another type of suitable absorbent nonwoven web is a coform material, which is typically a blend of cellulose fibers and meltblown fibers. The term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and so forth. Some examples of such coform materials are disclosed in U.S. Pat. Nos. 4,100,324 to Anderson, et al.; 5,284,703 to Everhart, et al.; and 5,350,624 to Georger, et al.; which are incorporated herein in their entirety by reference thereto for all purposes.

If desired, the absorbent nonwoven web may also contain a superabsorbent material. Superabsorbents have the ability to absorb a great amount of fluid in relation to their own weight. Typical superabsorbents used in sanitary napkins may absorb anywhere from about 5 to about 60 times their weight in blood. Superabsorbent materials are produced in a wide variety of forms including, but not limited to, particles, fibers and flakes. Superabsorbents having a high mechanical stability in the swollen state, an ability to rapidly absorb fluid, and those having a strong liquid binding capacity, typically perform well in absorbent articles. Hydroxy functional polymers have been found to be good superabsorbents for this application. For example, a hydrogel-forming polymer, such as a partially neutralized cross-linked copolymer of polyacrylic acid and polyvinyl alcohol, may be utilized. After the polymer is formed, it is mixed with about a 1% anhydrous citric acid powder. The citric acid has been found to increase the ability of the superabsorbent to absorb menses and blood. This is particularly beneficial for use in a sanitary napkin or other feminine pads. The finely ground, anhydrous citric acid powder, which is void of water, along with trace amounts of fumed silica, is mixed with the polymer that may have been screened to an appropriate particle size. This mixture may also be formed into a composite or a laminate structure. Such superabsorbents may be obtained from Dow Chemical and Stockhausen, Inc., among others. This superabsorbent is a partially neutralized salt of cross-linked copolymer of polyacrylic acid and polyvinyl alcohol having an absorbency under load value above about 25. Some suitable superabsorbents are described in U.S. Pat. Nos. 4,798,603 to Meyers. et al., Re. 32,649 to Brandt. et al. and 4,467,012 to Pedersen, et al., 4,604,313 and 4,655,757 to McFarland, et al., 6,387,495 to Reeves, et al., as well as in published European Patent Application 0,339,461 to Kellenberger.

As indicated above, the odor control composition may also be incorporated into a liquid transmissive layer of the absorbent article, such as the bodyside liner or surge layer. Such liquid transmissive layers are typically intended to transmit liquid quickly, and thus generally do not retain or absorb significant quantities of aqueous liquid. Materials that transmit liquid in such a manner include, but are not limited to, thermoplastic spunbonded webs, meltblown webs, bonded carded webs, air laid webs, and so forth. A wide variety of thermoplastic materials may be used to construct these non-retentive nonwoven webs, including without limitation polyamides, polyesters, polyolefins, copolymers of ethylene and propylene, copolymers of ethylene or propylene with a $C_4$-$C_{20}$ alpha-olefin, terpolymers of ethylene with propylene and a $C_4$-$C_{20}$ alpha-olefin, ethylene vinyl acetate copolymers, propylene vinyl acetate copolymers, styrene-poly(ethylene-alpha-olefin) elastomers, polyurethanes, A-B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, poly-1-butene, copolymers of poly-1-butene including ethylene-1-butene copolymers, polybutadiene, isobutylene-isoprene copolymers, and combinations of any of the foregoing.

The odor control composition, or the components thereof, may be applied to a substrate using any of a variety of well-known application techniques. Suitable application techniques include printing, dipping, spraying, melt extruding, solvent coating, powder coating, and so forth. The odor control composition may be incorporated within the matrix of the substrate and/or contained on the surface thereof. For example, in one embodiment, the odor control composition is coated onto one or more surfaces of the substrate. In one particular embodiment, a coating of the odor control composition may be "pattern printed" onto a substrate using printing techniques, such as flexographic printing, gravure printing, screen printing, or ink jet printing. Various examples of such printing techniques are described in U.S. Pat. No. 5,853,859 to Levy. et al. and U.S. Patent Application Publication No. 2004/0120904 to Lye, et al., which are incorporated herein in their entirety by reference thereto for all purposes.

The amount of the odor control composition present on the substrate may vary depending on the nature of the substrate and its intended application, the nature of the odor control composition, and so forth. For example, lower add-on levels may provide optimum absorbency or other characteristics of the substrate, while higher add-on levels may provide optimum odor reduction. Likewise, lower add-on levels may be more prevalent in circumstances when the odor control composition contains only a quinone compound. Nevertheless, the solids add-on level will generally range from about 0.001% to about 20%, in some embodiments from about 0.01% to about 10%, and in some embodiments, from about 0.05% to about 5%. The "solids add-on level" is determined by subtracting the weight of the untreated substrate from the weight of the treated substrate (after drying), dividing this calculated weight by the weight of the untreated substrate, and then multiplying by 100%.

Likewise, the percent coverage of the odor control composition on the surface of a substrate may be selectively varied to improve odor reduction. Typically, the percent coverage is greater than about 50%, in some embodiments greater than about 80%, and in some embodiments, approximately 100% of the area of a given surface. Even when uniformly present (e.g., about 100% coverage) on a surface, the substrate may still remain porous. For instance, the porosity of the coated substrate may enable it to still be used in application where liquid permeability is required, such as in absorbent articles. Also, the porosity of the coated substrate allows gaseous odorous compounds to flow therethrough, exposing the underside of the odor control composition (surface facing the substrate) to the odorous compound. In this manner, the entire surface area of the odor control composition is more effectively utilized for reducing odor. In most embodiments, the coated substrate exhibits a porosity such that about 20 cubic feet of air or greater may flow through 1 square foot of the substrate in 1 minute under an air pressure differential of 125 Pascals (0.5 inches of water). In other words, such a substrate is said to have an air permeability of about 20 cubic feet per minute (cfm) or greater. In some embodiments, the air permeability ranges from about 20 cfm to about 500 cfm, in some embodiments from about 50 cfm to about 400 cfm, and in some embodiments, from about 75 cfm to about 300 cfm, under an air pressure differential of 125 Pascals. Air permeability (volumetric air flow per square foot of material under an air pressure differential of 125 Pascals) may be measured in a variety of ways. For example, "Frazier Air Permeability" is determined according to Federal Test Standard 191A, Method 5450 with a Frazier Air Permeability Tester (Frazier Precision Instrument Co., Gaithersburg, Md.), and is reported as an average of 3 sample readings.

The nature of the odor control composition may vary depending on its intended use. For example, in some embodiments, the odor control composition may be a water-soluble powder. Due to its solubility in water, the powder may dissolve in the presence of aqueous-based odorous compounds, such as urine. In this manner, the powder uniformly disperses in the fluid so that higher concentrations of the odor-reducing compounds are placed in contact with the odorous compound. The dissolution of the powder also has an ancillary benefit of changing the color of the odorous compound, which may be more aesthetically pleasing to the consumer. In one embodiment, for instance, the odor control composition is a water-soluble anthraquinone powder, such as a powder of Acid Blue 25, Acid Green 41, Acid Blue 45, Mordant Violet 5, Acid Blue 129, Acid Green 25, or Acid Green 27. Such powders are commercially available from Sigma-Aldrich Chemical Co. of St. Louis, Mo. Other suitable water-soluble anthraquinone powders, such as D&C Green No. 5, are commercially available from Noveon Hilton Davis, Inc. of Cincinnati, Ohio. If desired, the powder may be applied to a substrate (e.g., layer of an absorbent article).

If desired, the odor control composition may also be an aqueous solution. Such aqueous solutions may optionally be applied to the substrate and then dried. The amount of the quinone compound in the aqueous solution may generally vary based on the level of odor control and optional color pattern or design utilized. For instance, in some embodiments, the quinone compound may comprise from about 0.001 wt. % to about 20%, in some embodiments from about 0.01 wt. % to about 15 wt. %, in some embodiments from about 0.1 wt. % to about 10 wt. %, in some embodiments from about 0.25 wt. % to about 5 wt. %, and in some embodiments, from about 0.5 wt. % to about 2 wt. % of the aqueous solution. Likewise, the amount of high-surface area particles in the aqueous solution may also vary. For instance, the high-surface area particles may comprise from about 0.1 wt. % to about 25%, in some embodiments from about 0.25 wt. % to about 15 wt. %, in some embodiments from about 0.5 wt. % to about 10 wt. %, in some embodiments from about 1 wt. % to about 5 wt. % of the aqueous solution.

The odor control composition of the present invention is versatile and may also be used with other types of articles of manufacture. For instance, the odor control composition may be used in air filters, such as house filters, vent filters, disposable facemasks, and facemask filters. Exemplary facemasks, for instance, are described and shown, for example, in U.S. Pat. Nos. 4,802,473; 4,969,457; 5,322,061; 5,383,450; 5,553,608; 5,020,533; 5,813,398; and 6,427,693, which are incorporated herein in their entirety by reference thereto for all purposes. In one embodiment, a substrate coated with the odor control composition of the present invention may be utilized as a filtration layer of the facemask. Filtration layers, such as meltblown nonwoven webs, spunbond nonwoven webs, and laminates thereof, are well known in the art.

The odor control composition may also be used in bedpans, nursing homes, etc. For example, an odor control powder may be used as a stand-alone product that is dissolvable in urine to reduce its odor. In another embodiment, the odor control composition may be used on walls, wallpaper, glass, toilets, and/or countertops. For instance, the odor control composition may be used in a restroom facility. Other uses include, without limitation, refrigerator mats and fabric softener sheets. The odor control composition may also be used in water treatment systems for removing compounds from well water or in toilet tanks to reduce the odors resulting from urine. The odor control composition may also be used in liquid detergents and household cleaners to remove odors. In another embodiment, the odor control composition is used as aerosol odor neutralizers/deodorants. The odor control composition is packaged with a propellant that allows spraying the odor control composition into the air for removal of gases and odorous compounds. The odor control composition may be used in a household air freshener or be used in combination with a mist emitted from a vaporizer or humidifier.

In still other embodiments, the odor control composition may be employed in conjunction with a garment. For instance, garments, such as meat and seafood packing industry aprons/attire, grocery store aprons, paper mill aprons/attire, farm/dairy garments, hunting garments, etc., may be incorporated with the odor control composition of the present invention. As an example, hunters often wear garments that are camouflaged for the particular hunting environment. The odor control composition of the present invention may thus be used to form the camouflage pattern. Specifically, the quinone compound may impart the desired color pattern and also help reduce human odor during hunting.

The effectiveness of the odor control composition of the present invention may be measured in a variety of ways. For example, the percent of an odorous compound adsorbed by the odor control composition may be determined using the headspace gas chromatography test as set forth herein. In some embodiments, for instance, the odor control composition of the present invention is capable of adsorbing at least about 25%, in some embodiments at least about 45%, and in some embodiments, at least about 65% of a particular odorous compound. The effectiveness of the odor control composition in removing odors may also be measured in terms of "Relative Adsorption Efficiency", which is also determined using headspace gas chromatography and measured in terms of milligrams of odor adsorbed per gram of the odor control composition. It should be recognized that the surface chemistry of any one type of odor control composition may not be suitable to reduce all types of odors, and that low adsorption of one or more odorous compounds may be compensated by good adsorption of other odorous compounds.

The present invention may be better understood with reference to the following examples.

Test Methods

Quantitative and qualitative tests were used in the Examples. Quantitative odor adsorption was determined in Example 9 using a test known as "Headspace Gas Chromatography." Headspace gas chromatography testing was conducted on an Agilent Technologies 5890, Series II gas chromatograph with an Agilent Technology 7694 headspace sampler (Agilent Technologies, Waldbronn, Germany). Helium was used as the carrier gas (injection port pressure: 12.7 psig; headspace vial pressure: 15.8 psig; supply line pressure is at 60 psig). A DB-624 column was used for the odorous compound that had a length of 30 meters and an internal diameter of 0.25 millimeters. Such a column is available from J&W Scientific, Inc. of Folsom, Calif.

The operating parameters used for the headspace gas chromatography are shown below in Table 1:

TABLE 1

Operating Parameters for the Headspace Gas Chromatography Device.
Headspace Parameters

| | | |
|---|---|---|
| Zone Temps, ° C. | Oven | 37 |
| | Loop | 42 |
| | TR. Line | 47 |
| Event Time, minutes | GC Cycle time | 10.0 |
| | Vial eq. Time | 10.0 |
| | Pressuriz. Time | 0.20 |
| | Loop fill time | 0.20 |
| | Loop eq. Time | 0.15 |
| | Inject time | 0.30 |
| Vial Parameters | First vial | 1 |
| | Last vial | 1 |
| | Shake | [off] |

The test procedure involved placing 82 milligrams (1"×2" strip) of a tissue wrap with a 7 wt. % coating of an odor-absorbing anthraquinone dye (0.1 wt. %) and Snowtex-AK colloidal nanoparticles (1.0 wt. %) in a 20-cubic centimeter headspace vial. Using a syringe, an aliquot of an odorous compound was also placed in the vial. Specifically, testing was done with 839 micrograms of ethyl mercaptan (1 microliter), 804 micrograms (1 microliter) of isovaleraldehyde, and 726 micrograms (1 microliter) of triethylamine (TEA). Each sample was tested in triplicate. The vial was then sealed with a cap and a septum and placed in the headspace gas chromatography oven at 37° C. After two (2) hours, a hollow needle was inserted through the septum and into the vial. A 1-cubic centimeter sample of the headspace (air inside the vial) was then injected into the gas chromatograph. Initially, a control vial with only the aliquot of odorous compound was tested to define 0% odorous compound adsorption. To calculate the amount of headspace odorous compound removed by the sample, the peak area for the odorous compound from the vial with the sample was compared to the peak area from the odorous compound control vial.

Qualitative odor reduction was also assessed against common odors, such as garlic and urine. Specifically, panelists assessed odorant-containing jars by carefully unscrewing, and then raising the lid of each jar in a controlled manner, such that the odor was not diluted by the ambient air. The jars were wrapped and coded to ensure that the sample identity was unknown.

EXAMPLE 1

The ability to coat a quinone compound onto a paper towel was demonstrated. Specifically, D&C Green No. 5 was initially dissolved into 1 liter of deionized water to form five sample solutions (Samples 2-6), wherein the concentration of D&C Green No. 5 varied from 0.001 wt. %, 0.01 wt. %, 0.1 wt. %, 0.25 wt. %, and 0.5 wt. %, respectively. Each solution also contained 1 wt. % of Snowtex AK (SN-AK) particles, which are colloidal silica nanoparticles coated with alumina and commercially available from Nissan Chemical America of Houston, Tex. The particles have an average particle size of between 10 to 20 nanometers and a surface area between 180 to 240 square meters per gram. A solution of only 1 wt. % of SN-AK particles was also formed as a control (Sample 1). Scott® paper towels (commercially available from Kimberly-Clark Corp.) were weighed, oven-dried overnight at 90° C., and weighed again the next day to calculate the amount of residual water in each towel. The towels were then dipped into each solution and hung to dry overnight, after which they were weighed again. The treated towels were then rinsed in deionized water to remove any unbound dye and hung again to dry overnight. After weighing the treated towels, they were once again oven-dried overnight at 90° C. and weighed to determine the dry add-on percentages (100×[dry weight final/dry weight initial]).

The resulting add-on percentages for Samples 1-6 were 5.7%±1.8%, 4.8%±1.3%, 4.3%±0.9%, 7.0%±1.2%, 2.8%±0.8%, and 0.9%±0.8%, respectively. The difference between the add-on level of Sample 1 (the control sample) and Samples 2-3 (0.001 wt. % and 0.01 wt. % D&C Green No. 5) was not significant. The highest add-on was achieved for Sample 4, which utilized 0.1 wt. % D&C Green No. 5. However, the add-on level decreased in Samples 5-6 when the concentration of dye was further increased. Without intending to be limited by theory, it is believed that higher dye concentrations may make it more difficult for the SN-AK particles to bind to the paper towel. Thus, the coating contains more dye particles than SN-AK-bound dye particles, thereby resulting in a lighter towel and a lower add-on percentage. Nevertheless, because the dye particles weigh considerably less than the SN-AK particles, the add-on level of the dye alone is inherently difficult to calculate.

EXAMPLE 2

The effectiveness of a quinone dye in reducing garlic odor was demonstrated. Initially, strips of each treated towel of Example 1 (Samples 2-6) were cut and placed in a jar with approximately 125 milligrams of freshly cut garlic. A strip from an uncoated Scott® paper towel (Sample 7), as well as the control towel of Example 1 (Sample 1), were also tested as controls. Garlic odor was assessed by a panel of individuals at intervals of 3, 19, 27, 41, and 121 hours. A score of "7" was assigned to the most malodorous jar and a score of "1" was assigned to the least malodorous jar. The results are shown in FIG. 1.

As shown, a line is drawn in FIG. 1 at the score of "4" to represent the level at which garlic malodor was perceived to be most dramatically reduced. The control samples did not reduce garlic odor and received almost unanimous scores of either 6 or 7. The dye concentrations of 0.1 wt. %, 0.25 wt. %, and 0.5 wt. % (Samples 4-6) were shown to be the most efficacious in removing garlic odor. The behavior of Samples 2-3 (0.001 wt. % and 0.01 wt. % D&C Green No. 5) was found to be time-dependent. Specifically, these treatments were not initially efficacious in removing garlic odor, but seemed to improve as time increased. However, after 121 hours, the treatments no longer reduced garlic malodor, indicating that their capacity had been exceeded.

EXAMPLE 3

The effectiveness of a quinone dye in reducing urine odor was demonstrated. Initially, strips of treated towels of Example 1 (Samples 2-4 and 6) were cut to the same size as the pledgefte area of a Poise® pad (commercially available from Kimberly-Clark Corp.). A strip from an uncoated Scott® paper towel (Sample 7), as well as the control towel of Example 1 (Sample 1), were also tested as controls. Poise® pads were then cut open, and the paper towel strips were placed within the tissue-wrap area. Thereafter, the tissue was rewrapped and the pad reassembled. The pads were placed in randomly labeled mason jars for testing with urine odor. Human female urine was then collected and pooled by a nurse on staff at Kimberly-Clark Corporation. The pooled urine was added to each pad in 50-milliliter aliquots using an automated pipette aid. The pads were allowed to soak in the urine at 37° C. and urine odor was assessed by a panel of individuals after 6, 24, and 30 hours. A score of "6" was assigned to the most malodorous jar and a score of "1" was assigned to the least malodorous jar. The results are shown in FIG. 2.

Figure 2:
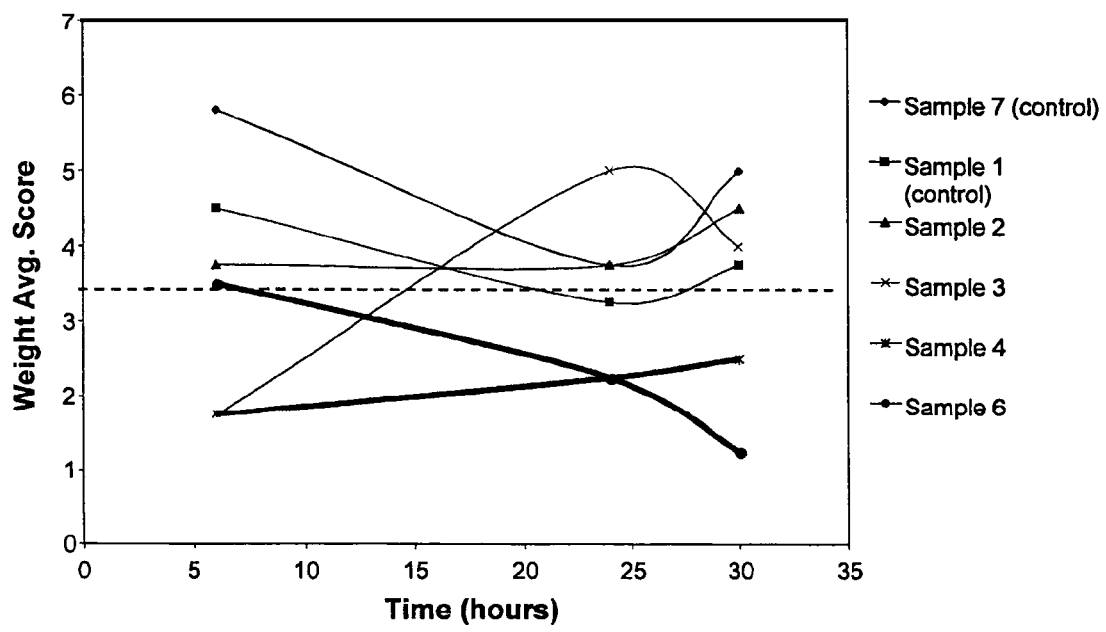
FIG. 2 is a graphical depiction of the results of Example 3, in which the average urine odor control ranking is plotted versus time (hours).

As shown, a line is drawn in FIG. 2 at the score of about "3.5" to represent the level at which urine malodor was perceived to be most dramatically reduced. The control samples were consistently perceived as having the most urine malodor. On the other hand, Samples 4 and 6 were consistently judged to have the least urine malodor. Interestingly, Sample 3 was initially thought to be very good against urine odor, but could not sustain this behavior over time. Without intending to be limited by theory, it is believed that the reason for this behavior relates to the relatively low level of urine odor present after 6 hours. Such a low level of odor presents some complications in assessment as it can be very difficult for panelists to rank very minimal odors (the odors tend to seem very similar).

EXAMPLE 4

The effectiveness of a quinone dye in reducing urine odor was demonstrated. Specifically, D&C Green No. 5 was initially dissolved into 1 liter of deionized water to form five sample solutions (Samples 9-12), wherein the concentration of D&C Green No. 5 varied from 0.01 wt. %, 0.1 wt. %, 0.25 wt. %, and 0.5 wt. %, respectively. Each solution also contained 1 wt. % of Snowtex AK (SN-AK) particles, which are colloidal silica nanoparticles coated with alumina and commercially available from Nissan Chemical America of Houston, Tex. The particles have an average particle size of between 10 to 20 nanometers and a surface area between 180 to 240 square meters per gram. A solution of only 1 wt. % of SN-AK particles was also formed as a control (Sample 8). Samples of tissue wrap were formed by cutting 9"×6" sheets from a roll of tissue (1 ply white cellulose wrap sheet having a basis weight of 16.6 grams per square meter). Samples were weighed and oven-dried overnight at 90° C., then weighed again the next day to calculate the amount of residual water in each wrap. The wraps were then dipped into each solution and hung to dry overnight, after which they were weighed again. The treated wraps were then rinsed in deionized water to remove any unbound dye and hung again to dry overnight. After weighing the treated wraps, they were once again oven-dried overnight at 90° C. and weighed to determine the dry add-on percentages (100×[dry weight final/dry weight initial]).

The resulting add-on percentages for Samples 8-12 were 7.9%±1.3%, 6.8%±0.7%, 8.0%±5.1%, 1.3%±2.9%, and 3.2%±1.5%, respectively. The difference between the add-on level of Sample 8 (the control sample) and Samples 9 (0.01 wt. % D&C Green No. 5) was not significant. The add-on levels were roughly equivalent for each sample, except for Samples 11 and 12. Without intending to be limited by theory, it is believed that higher dye concentrations make it more difficult for the SN-AK particles to bind to the paper towel. Thus, the coating contains more dye particles than SN-AK-bound dye particles, thereby resulting in a lighter towel and a lower add-on percentage. Because the dye particles weigh considerably less than the SN-AK particles, the add-on level of the dye alone is inherently difficult to calculate. In addition, the standard deviation for the 0.1% coated materials was relatively high. When wet, the tissue wrap was extremely hard to handle and samples become fragile. This particular set may have been ripped, torn, or coated more unevenly than the others.

Once formed, the samples were put into Poise® pads (commercially available from Kimberly-Clark Corp.) by carefully tearing away the tissue wrap surrounding the pledgette within the pads, rewrapping the pledgette with the samples, and then reconstructing the pad. An untreated Poise® pad (Sample 13) was used as one control. In addition, an untreated Poise® pad (Sample 13) was used as one control. Further, a Poise® pad with an activated carbon ink treated tissue wrap around the pledget (Sample 14) was also used for comparison. The activated carbon ink was obtained from MeadWestvaco Inc. of Covington, Va. under the name "NUCHAR PMA." The ink is believed to contain 14-16 wt. % activated carbon, 11-14 wt. % styrene-acrylic copolymer, and 70-75 wt. % water. The activated carbon ink was gravure printed onto a corona-treated polyethylene film (10.7 wt. % ink). Further, the ink was also applied to a cellulose tissue wrap (1 ply white cellulose wrap having a basis weight of 16.6 grams per square meter) using the "dip and squeeze" method, followed by drying over steam cans. The resulting ink had a basis weight of 5 to 8 grams per square meter. Serenity® Night & Day™ incontinence pads, which are commercially available from SCA Incontinence Care of Eddystone, Pa. and said to employ OdaSorb Plus™ to reduce odor, were also used for comparison (Sample 15).

The pads were placed in randomly labeled mason jars for testing with urine odor. Human female urine was then collected and pooled by a nurse on staff at Kimberly-Clark Corporation. The pooled urine was then either added to each pad in 50-milliliter aliquots using an automated pipette aid, or it was aged overnight at 37° C. and then added to each pad. The pads receiving the fresh urine were placed in a incubator overnight at 37° C. and urine odor was assessed by a panel of individuals after 24 hours. The pads receiving the pre-incubated urine were allowed to react for 5 additional hours in the incubator before assessment (i.e., total of 29 hours). A score of "8" was assigned to the most malodorous jar and a score of "1" was assigned to the least malodorous jar. The results are shown in Tables 2-3. The averages for each group are also set forth in Table 4.

TABLE 2

Odor rankings for Samples 8-15 (applied with fresh urine)

| Sample | Ranking (number of panelists) | | | | | | | |
|---|---|---|---|---|---|---|---|---|
| | 1 | 2 | 3 | 4 | 5 | 6 | 7 | 8 |
| 8 (control) | — | — | — | — | 1 | 2 | 2 | — |
| 9 | — | — | — | — | — | 2 | 1 | 2 |
| 10 | 1 | 3 | — | — | 1 | — | — | — |
| 11 | — | — | 3 | 1 | 1 | — | — | — |
| 12 | — | 1 | 2 | 1 | 1 | — | — | — |
| 13 (control) | — | — | — | — | 1 | — | 2 | 2 |
| 14 (comparative) | 4 | — | — | 1 | — | — | — | — |
| 15 (comparative) | — | 1 | — | 2 | — | 1 | — | 1 |

TABLE 3

Odor rankings for Samples 8-5 (applied with pre-incubated urine)

| Sample | Ranking (number of panelists) | | | | | | | |
|---|---|---|---|---|---|---|---|---|
| | 1 | 2 | 3 | 4 | 5 | 6 | 7 | 8 |
| 8 (control) | — | — | — | 1 | 1 | 1 | — | 2 |
| 9 | — | — | — | — | — | 3 | 2 | — |
| 10 | 1 | 2 | 1 | — | 1 | — | — | — |
| 11 | 1 | 1 | — | 2 | 1 | — | — | — |
| 12 | — | 1 | 2 | 1 | 1 | — | — | — |
| 13 (control) | — | — | — | — | — | — | 2 | 3 |
| 14 (comparative) | 1 | — | 1 | — | 2 | — | 1 | — |
| 15 (comparative) | 2 | 1 | — | 1 | — | 1 | — | — |

TABLE 4

Average Odor rankings

| Fresh Urine | | Pre-Incubated Urine | |
|---|---|---|---|
| Sample | Avg. Ranking | Sample | Avg. Ranking |
| 8 (control) | 6.2 | 8 (control) | 6.2 |
| 9 | 7.0 | 9 | 6.4 |
| 10 | 2.4 | 10 | 2.6 |
| 11 | 3.6 | 11 | 3.1 |
| 12 | 3.4 | 12 | 3.0 |
| 13 (control) | 7.0 | 13 (control) | 7.6 |
| 14 (comparative) | 1.6 | 14 (comparative) | 2.8 |
| 15 (comparative) | 4.8 | 15 (comparative) | 4.2 |

As shown, Sample 9 was almost equally effective as activated carbon in reducing odor. Moreover, the dye-containing samples are an aesthetically pleasing alternative to the black color of activated carbon, and allows for the possibility of colored patterns or designs.

EXAMPLE 5

The effectiveness of various quinone dyes in reducing urine odor was compared. Human female urine was initially collected and pooled by a nurse on staff at Kimberly-Clark Corporation. The pooled urine was added to mason jars in 50-milliliter aliquots using an automated pipette aid. Powders of Acid Blue 129 and Acid Green 27 (commercially available from Sigma-Aldrich Chemical Co., Inc. of St. Louis, Mo.), as well as D&C Green No. 5 (commercially available from Noveon Hilton Davis, Inc. of Cincinnati, Ohio), were then weighed and placed into the mason jars containing 50 milliliters of urine so that the final concentration of the dye powder was 8 millimolar (equivalent to 0.5 wt. %). The mason jars were placed in an incubator overnight at 37° C. and urine odor was assessed by a panel of individuals after 6 and 24 hours. A score of "10" was assigned to the most malodorous jar and a score of "1" was assigned to the least malodorous jar. The results are shown in Tables 5-6. The averages for each group are also set forth in Table 7.

TABLE 5

Odor rankings After 6 Hours

| Sample | Ranking (number of panelists) | | | | | | | | | |
|---|---|---|---|---|---|---|---|---|---|---|
| | 1 | 2 | 3 | 4 | 5 | 6 | 7 | 8 | 9 | 10 |
| Urine (control) | — | — | — | — | — | — | — | — | — | 5 |
| Acid Green 27 | — | — | — | 3 | 2 | — | — | — | — | — |
| D&C Green No. 5 | 1 | — | 3 | — | 1 | — | — | — | — | — |
| Acid Blue 129 | 4 | — | — | 1 | — | — | — | — | — | — |

TABLE 6

Odor rankings After 24 Hours

| Sample | Ranking (number of panelists) | | | | | | | | | |
|---|---|---|---|---|---|---|---|---|---|---|
| | 1 | 2 | 3 | 4 | 5 | 6 | 7 | 8 | 9 | 10 |
| Urine (control) | — | — | — | — | — | — | — | — | — | 6 |
| Acid Green 27 | 1 | — | 2 | — | — | — | 3 | — | — | — |
| D&C Green No. 5 | — | — | — | 3 | 1 | — | 2 | — | — | — |
| Acid Blue 129 | 5 | — | 1 | — | — | — | — | — | — | — |

TABLE 7

Average Odor rankings

| After 6 Hours | | After 24 Hours | |
|---|---|---|---|
| Sample | Avg. Ranking | Sample | Avg. Ranking |
| Urine | 10.0 | Urine | 10.0 |
| Acid Green 27 | 4.4 | Acid Green 27 | 4.5 |
| D&C Green No. 5 | 3.0 | D&C Green No. 5 | 5.2 |
| Acid Blue 129 | 1.6 | Acid Blue 129 | 1.3 |

As indicated, Acid Blue 129, D&C Green No. 5, and Acid Green 27 functioned effectively in reducing urine malodor.

EXAMPLE 6

The effectiveness of various dyes in reducing urine odor was compared. The dyes chosen for this example were powders of Acid Blue 25, Acid Blue 45, Acid Blue 129, FD&C Blue No. 1 (a triarylmethane dye), Acid Green 27, Acid Green 41, and Mordant Violet 5 (Alizarin Violet 3R) (commercially available from Sigma-Aldrich Chemical Co., Inc. of St. Louis, Mo.), as well as D&C Green No. 5 (commercially available from Noveon Hilton Davis, Inc. of Cincinnati, Ohio). Human female urine was initially collected and pooled by a nurse on staff at Kimberly-Clark Corporation. The pooled urine was added to mason jars in 50-milliliter aliquots using an automated pipette aid. Powders of the aforementioned dyes were weighed and placed into the mason jars containing 50 milliliters of urine so that the final concentration of the dye powder was 1.6 millimolar (equivalent to 0.1 wt. %). The mason jars were placed in an incubator overnight at 37° C. and urine odor was assessed by a panel of individuals after 24 hours. A score of "10" was assigned to the most malodorous jar and a score of "1" was assigned to the least malodorous jar. The results from this study indicated that the 1.6-millimolar concentration of anthraquinone powders dissolved in urine were not optimal for the evaluation of odor control behavior.

Nevertheless, it was observed that Mordant Violet 5 did not perform as well in reducing odor as D&C Green No. 5. These dyes are structural isomers, i.e., the sulfonic acid-containing phenyl rings are in a cis-conformation for the D&C Green No. 5 and in a trans-conformation for the Mordant Violet 5. Consequently, D&C Green No. 5 is substituted at positions 1 and 4 (the "second" anthraquinone ring), while Mordant Violet 5 is substituted at positions 1 and 5 (both the "first" and "second" anthraquinone rings). Without intending to be limited by theory, it is believed that the odor control properties of the dye may be improved if positions 5 through 8 of the anthraquinone structure (the "first" anthraquinone ring) are unsubstituted.

EXAMPLE 7

The effectiveness of various dyes in reducing urine odor was compared. The dyes chosen for this example were Acid Blue 25, Acid Blue 45, Acid Blue 129, FD&C Blue No. 1 (triarylmethane dye), Acid Green 25, Acid Green 27, Acid Green 41, Mordant Violet 5 (Alizarin Violet 3R), 1,2 naphthaquinone-2-sulfonic acid potassium salt, and 1,4 naphthaquinone-2-sulfonic acid potassium salt. Human female urine was initially collected and pooled by a nurse on staff at Kimberly-Clark Corporation. The pooled urine was added to mason jars in 50-milliliter aliquots using an automated pipette aid. Powders of the aforementioned dyes (commercially available from Sigma-Aldrich Chemical Co., Inc. of St. Louis, Mo. and Noveon Hilton Davis, Inc. of Cincinnati, Ohio) were weighed and placed into the mason jars containing 50 milliliters of urine so that the final concentration of the dye powder was 8 millimolar (equivalent to 0.5 wt. %). The mason jars were placed in an incubator overnight at 37° C.

To aid in the assessment of the dyes, the mason jars were divided into two groups for a morning assessment, and the best of both groups were compared in an afternoon assessment (after a total of 24 hours). In addition to ranking the jars from least to most malodorous (on a scale from 1 to 7, with 7 being the most malodors), panelists were also asked to judge whether there were secondary (non-urine) odors present and, if so, the extent that the secondary odors were unpleasant (on a scale from 1 to 5, with 5 being extremely unpleasant).

The results for the first grouping are set forth below in Tables 8 and 9.

TABLE 8

Odor Control Rankings (First Grouping)

| Sample | Urine Odor Ranking (number of panelists) | | | | | | | Secondary Odor Ranking |
|---|---|---|---|---|---|---|---|---|
| | 1 | 2 | 3 | 4 | 5 | 6 | 7 | |
| Pure Urine | — | — | 1 | — | — | 1 | 3 | — |
| Alizarin Violet 3R | — | — | — | 1 | — | 3 | 1 | 1 |
| 1,2 Naphthaquinone | — | 1 | 2 | 1 | — | — | 1 | 4, 5, 2 |

TABLE 8-continued

Odor Control Rankings (First Grouping)

| Sample | Urine Odor Ranking (number of panelists) | | | | | | | Secondary Odor Ranking |
|---|---|---|---|---|---|---|---|---|
| | 1 | 2 | 3 | 4 | 5 | 6 | 7 | |
| Acid Blue 25 | 1 | 1 | 1 | 1 | 1 | — | — | 2 |
| Acid Green 25 | 3 | 1 | — | — | — | 1 | — | 1, 1, 4, 1, 1 |
| Acid Green 41 | 1 | 2 | 1 | 1 | — | — | — | 1 |
| FD&C Blue No. 1 | — | — | — | 1 | 4 | — | — | 3 |

TABLE 9

Average Urine Odor Ranking (First Grouping)

| Sample | Avg. Score |
|---|---|
| Pure Urine | 6.0 |
| Alizarin Violet 3R | 5.8 |
| 1,2 Naphthaquinone | 3.8 |
| Acid Blue 25 | 3.0 |
| Acid Green 25 | 2.2 |
| Acid Green 41 | 2.4 |
| FD&C Blue No. 1 | 4.8 |

In this first grouping, Acid Blue 25, Acid Green 25, and Acid Green 41 all functioned effectively to reduce odor. Although the majority of panelists felt that Acid Green 25 had a secondary odor, it was not found to be unpleasant by most panelists. That is, comments regarding this odor ranged from "slightly chemical", "dirt-like", "earthy", or "damp." In addition, 1,2-naphthaquinone also effectively reduced urine odor, although an unpleasant secondary smell was found to be present.

The results for the second grouping are set forth below in Tables 10 and 11.

TABLE 10

Odor Control Rankings (Second Grouping)

| Sample | Urine Odor Ranking (number of panelists) | | | | | | Secondary Odor Ranking |
|---|---|---|---|---|---|---|---|
| | 1 | 2 | 3 | 4 | 5 | 6 | |
| Pure Urine | — | — | — | — | — | 5 | — |
| Acid Blue 45 | — | 1 | 2 | 1 | 1 | — | 4, 4 |
| 1,4 Naphthaquinone | 2 | 2 | 1 | — | — | — | 5, 3, 5, 4 |
| Acid Blue 129 | 3 | — | 2 | — | — | — | 1, 3 |
| Acid Green 27 | — | 2 | — | 1 | 2 | — | 2 |
| D&C Green No. 5 | — | — | — | 3 | 2 | — | 4 |

TABLE 11

Average Urine Odor Ranking (Second Grouping)

| Sample | Avg. Score |
|---|---|
| Pure Urine | 6.0 |
| Acid Blue 45 | 3.4 |
| 1,4 Naphthaquinone | 1.8 |
| Acid Blue 129 | 1.8 |
| Acid Green 27 | 3.6 |
| Acid Green 25 | 4.4 |

In this second grouping, D&C Green No. 5 did not perform as well compared to the other dyes. The naphthaquinone compound was again found to have an unpleasant secondary odor. Acid Green 25 and D&C Green 25 have the same structure, but a slightly different purity level, i.e., D&C Green No. 5 is 89% pure and Acid Green 25 is 75% pure. It is possible that the performance of Acid Green 25 (Group 1) is a result of impurities in the compound, such as those that are anthraquinone in nature.

In the afternoon, panelists were asked to assess the top performers in both groupings as a single group. In this assessment, panelists were given instructions to rank the least malodorous jar as "1" and the most malodorous jar as "10," remaining free to rank the other jars between 2-9. This type of ranking was chosen to obtain an idea of how much separation existed between the best and second best compounds, as well as how much worse the most malodorous compound is from the second most malodorous compound. The results are shown in Tables 12-14 (Table 14 shows the average urine odor rankings ignoring statistical anomalies).

TABLE 12

Odor Control Rankings (After 24 Hours)

| Sample | Urine Odor Ranking (number of panelists) | | | | | | | | | | Secondary Odor Ranking |
|---|---|---|---|---|---|---|---|---|---|---|---|
| | 1 | 2 | 3 | 4 | 5 | 6 | 7 | 8 | 9 | 10 | |
| Pure Urine | — | — | — | — | — | — | — | 2 | 1 | 2 | 5 |
| Acid Blue 25 | — | — | — | 1 | — | — | 1 | — | 2 | 1 | 4 |
| Acid Green 25 | 3 | 1 | — | — | — | — | — | — | — | 1 | 1, 1, 4, 1, 2 |
| Acid Green 41 | 1 | 2 | 1 | — | — | — | 1 | — | — | — | 1, 3, 2 |
| Acid Blue 129 | 1 | — | 1 | 1 | 1 | 1 | — | — | — | — | 4, 5 |
| Acid Green 27 | — | 1 | — | — | — | — | 2 | 1 | 1 | — | 4 |
| D&C Green No. 5 | — | 1 | — | 1 | — | — | 2 | — | — | 1 | 4 |

TABLE 13

Average Urine Odor Ranking

| Sample | Avg. Score |
|---|---|
| Pure Urine | 9.0 |
| Acid Blue 25 | 6.8 |
| Acid Green 25 | 3.0 |
| Acid Green 41 | 3.0 |
| Acid Blue 129 | 3.8 |
| Acid Green 27 | 6.4 |
| D&C Green No. 5 | 6.0 |

TABLE 14

Average Urine Odor Ranking (with statistical corrections)

| Sample | Avg. Score |
|---|---|
| Pure Urine | 9.0 |
| Acid Blue 25 | 8.8 |
| Acid Green 25 | 1.3 |
| Acid Green 41 | 2.0 |
| Acid Blue 129 | 3.8 |
| Acid Green 27 | 8.8 |
| D&C Green No. 5 | 7.0 |

As indicated, Acid Green 25, Acid Green 41 and Acid Blue 129 achieved the best odor reduction.

EXAMPLE 8

The effectiveness of various quinone dyes in reducing urine odor was demonstrated. Specifically, Acid Green 25, Acid Green 41, Acid Blue 129, and D&C Green No. 5 were tested. Powders of the aforementioned dyes (commercially available from Sigma-Aldrich Chemical Co., Inc. of St. Louis, Mo. and Noveon Hilton Davis, Inc. of Cincinnati, Ohio) were dissolved in water so that the concentration of the dye was 8 millimolar (equivalent to 0.5 wt. %). Samples of tissue wrap were created by cutting 9"×6" sheets from a roll of tissue (1 ply white cellulose wrap sheet having a basis weight of 16.6 grams per square meter) were weighed, oven-dried overnight at 90° C., and weighed again the next day to calculate the amount of residual water in each wrap. The wraps were then dipped into a respective dye solution and hung to dry overnight, after which they were weighed again. The treated wraps were then rinsed in deionized water to remove any unbound dye and hung again to dry overnight. After weighing the treated wraps, they were once again oven-dried overnight at 90° C. and weighed to determine the dry add-on percentages (100×[dry weight final/dry weight initial]). The add-on percentage for each sample was approximately 1.6 wt. %.

Two different sets of Poise® pads (commercially available from Kimberly-Clark Corp.) were tested. The first set of dye-coated tissue wraps (without SN-AK) was inserted around the pledgette area of the Poise® pads. The Poise® pads were cut open and the tissue wrap surrounding the pledgette carefully removed and replaced with dye-coated tissue wrap. The second set of dye-coated tissue wraps (without SN-AK) used dye coatings on the top of the pad (rather than inside). These pads were constructed by spreading the solution over the top of each pad. To prevent the superabsorbent area of the pad from soaking up the solution, the pads were cut open prior to coating and a layer of plastic wrap was placed between the top layer of the pad and the superabsorbent core. A pad that was cut open, but coated only with water on top, was used as a control. All pads were dried at room temperature overnight before placing them in mason jars for testing. For control purposes, a Poise® pad was also tested that was cut open, but retained its original tissue wrap. In addition, Serenity® Night & Day™ incontinence pads, which are commercially available from SCA Incontinence Care of Eddystone, Pa. and said to employ OdaSorb Plus™ to reduce odor, were also used for comparison.

Fresh human female urine was then pooled, and 50-milliliter aliquots were applied to the pads using a pipette. The mason jars were placed in a 37° C. incubator overnight for assessment the next day. Upon assessment by panel members, it was determined that Acid Green 25 and Acid Green 41 performed best for the second set of pads, while Acid Green 25, Acid Green 41, and Acid Blue 129 performed best for the first set of pads. The jars were pooled together for a final assessment to determine the compounds and coating methodology that were the most effective. Panelists were again asked to rank any secondary odors for unpleasantness on a scale of 1-5. The results are shown in Tables 15 and 16.

TABLE 15

Odor Control Rankings (After 30 Hours)

| Sample | Urine Odor Ranking (number of panelists) | | | | | | | | Secondary Odor Ranking |
|---|---|---|---|---|---|---|---|---|---|
| | 1 | 2 | 3 | 4 | 5 | 6 | 7 | 8 | |
| Poise ® pad (1$^{st}$ set) (control) | — | 2 | — | — | — | 2 | — | — | 1 |
| Poise ® pad (2$^{nd}$ set) (control) | — | — | — | — | — | 1 | 3 | — | — |
| Serenity ® (comparative) | — | — | — | — | — | — | — | 4 | 5 |
| Acid Green 41 (2$^{nd}$ set) | — | 2 | 1 | 1 | — | — | — | — | 1 |
| Acid Blue 129 (1$^{st}$ set) | 1 | — | 1 | 2 | — | — | — | — | — |
| Acid Green 25 (1$^{st}$ set) | — | — | 1 | 1 | 1 | 1 | — | — | 4 |
| Acid Green 25 (2$^{nd}$ set) | 3 | — | — | — | — | — | 1 | — | — |

TABLE 16

Average Urine Odor Ranking

| Sample | Avg. Score | Std. Dev |
|---|---|---|
| Poise ® (1$^{st}$ set) | 4.00 | 2.30 |
| Poise ® (2$^{nd}$ set) | 6.75 | 0.50 |
| Serenity ® | 8.00 | 0.00 |
| Acid Green 41 (2$^{nd}$ set) | 2.75 | 0.96 |
| Acid Green 25 (2$^{nd}$ set) | 2.50 | 3.00 |
| Acid Blue 129 (1$^{st}$ set) | 3.00 | 1.40 |
| Acid Green 41 (1$^{st}$ set) | 4.50 | 1.00 |
| Acid Green (1$^{st}$ set) | 4.50 | 1.30 |
| Pure Urine | 9.00 | 9.00 |

Acid Green 25, when used as a top-sheet coating, was found to be the best performer overall, followed by Acid Green 41 (also as a top-sheet coating). Acid Blue 129 (tissue-wrap coating) also performed very well.

EXAMPLE 9

The effectiveness of various quinone dyes in reducing urine odor was quantitatively demonstrated. An exploratory study using Solid Phase MicroExtraction (SPME) was used to demonstrate urine odor reduction and identify the "odor finger print" changes caused by the use of quinone dyes. The GC/MS analysis conditions used for quantitation were:

| Instrument: | Agilent Technologies 5973N GC/MS |
| --- | --- |
| Column: | J&W DB-35MS (s/n US4568641H) |
| | (30 m, 0.25 mm ID, 0.25 u film.) |

Oven Program:

| Level | Rate (° C./min) | Final Temp.(° C.) | Final Time (min) |
| --- | --- | --- | --- |
| initial | | 40 | 1 |
| 1 | 5 | 100 | 0 |
| 2 | 10 | 200 | 0 |
| 3 | 15 | 300 | 0 |

| Carrier Gas: | Helium, 2.0 ml/minute (constant flow) |
| --- | --- |
| Injector: | Split 5:1 @ 250° C. |
| Detector: | GC/MS |
| | Source Temp: 230° C. |
| | Quad Temp: 150° C. |
| | Interface: 250° C. |
| | EM: 1188 v. |
| | HED: 10000 v. |
| | Threshold: 200 Samples: $2^2$ |
| | Scan: 33-250 Da |

Human female urine was collected and pooled by a nurse on staff at Kimberly-Clark. Aliquots of the urine (10 milliliters) were added to GC headspace vials containing Acid Green 25, D&C Green No. 5, Acid Blue 129 or Acid Green 41 powders so that the final concentration of the dye was 8 millimolar. A vial of pure urine was employed as a control sample. The vials were sealed by crimping and incubated overnight at 37° C. The samples were then exposed to a Solid Phase Microextraction (SPME) assembly for about 30 minutes to collect the volatiles for analysis. The SPME assembly employed a manual fiber holder (Supelco catalog No. 57330-U) and 85-μm carboxen/polydimethylsilicone (Supelco catalog No. 57334-U) on StableFlex fiber. Each vial was compared to the urine control, which contained no dye. All of the anthraquinone dyes in the study had similar reductions in the same peaks of the urine odor. Significant reduction was observed in the ketones (2- and 4-heptanone), dimethylsulfide, indole, thymol and menthol peaks.

EXAMPLE 10

The ability to print odor-reducing anthraquinone dyes in a variety of colors and designs was demonstrated. Specifically, a set of anthraquinone dyes were formulated into an ink-jet formulation by mixing 40 milliliters of a dye solution in deionized water (5 wt. % dye), 3 milliliters of ethylene glycol, 1.5 milliliters of glycerol, 3 milliliters of polyethylene glycol (MW=200), 1.5 milliliters of 1,3-propanediol, and 0.05 milliliters Surfynol™ 465. The anthraquinone and naphthaquinone dyes formulated into ink-jet ink formulations were D&C Green No. 5, Acid Green 41, Acid Blue 129, carminic acid (red), and 1,4-naphthaquinone-2-sulphonic acid (yellow). Each formulation was loaded separately into 30-milliliter margarita cartridges, which are commercially available from MacDermid ColorSpan Inc. of Edie Prairie, Minn. The cartridges were then loaded into Colorspan wide format ink-jet printers (McDermid Colorspan) for printing onto Scott® paper towels and wire-textured coform laminate (WTCL) substrates. The print obtained had excellent sharpness of print image and resolution.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An article of manufacture comprising a fibrous substrate, said fibrous substrate containing an odor control composition, wherein said odor control composition comprises high-surface area particles bonded with an odor-reducing quinone compound, the high surface area particles comprising silica, alumina, or combinations thereof and having an average size of less than 100 nanometers and a surface area from about 50 square meters per gram to about 600 square meters per gram, the odor control composition configured to adsorb at least one odorous compound wherein said odor-reducing quinone compound is obtained from a dye selected from the group consisting of Acid Blue 25, Acid Green 41, Acid Blue 45, Mordant Violet 5, Acid Blue 129, Acid Green 25, D&C Green No. 5, Acid Green 27, and combinations thereof.

2. The article of claim 1, wherein said odor-reducing composition further includes compounds is selected from the group consisting of anthraquinones, naphthaquinones, benzoquinones, hydroquinones, and combinations thereof.

3. The article of claim 1, wherein at least one ring of said anthraquinone is unsubstituted with functional groups.

4. The article of claim 1, wherein said odor-reducing quinone compound has a redox potential of less than −50 millivolts.

5. The article of claim 1, wherein said odor-reducing quinone compound has a redox potential of less than −150 millivolts.

6. The article of claim 1, wherein said odor-reducing quinone compound has a redox potential of less than −300 millivolts.

7. The article of claim 1, wherein said high-surface area particles have a pore volume of less than 0.5 milliliters per gram.

8. The article of claim 1, wherein said high-surface area particles have a positive zeta potential.

9. The article of claim 1, wherein said fibrous substrate comprises a nonwoven, woven, or paper web.

10. The article of claim 1, wherein the article is an absorbent article.

11. An absorbent article comprising at least one liquid transmissive layer and a liquid absorbent core, wherein said liquid-transmissive layer, said liquid-absorbent core, or combinations thereof, contain an odor control composition, said odor control composition comprising an odor-reducing quinone compound bonded with high surface area particles, the high surface area particles comprising silica, alumina, or combinations thereof and having an average size of less than 100 nanometers and a surface area from about 50 square meters per gram to about 600 square meters per gram, the odor control composition configured to adsorb at least one odorous compound wherein said odor-reducing quinone compound is obtained from a dye selected from the group consisting of Acid Blue 25, Acid Green 41, Acid Blue 45, Mordant Violet 5, Acid Blue 129, Acid Green 25, D&C Green No. 5, Acid Green 27, and combinations thereof.

12. The absorbent article of claim 11, wherein positions 5 through 8 of said anthraquinone are unsubstituted with functional groups.

13. The absorbent article of claim 11, wherein said odor-reducing quinone compound has a redox potential of less than −50 millivolts.

14. The absorbent article of claim 11, wherein said odor-reducing quinone compound has a redox potential of less than −150 millivolts.

15. The absorbent article of claim 11, wherein said odor-reducing quinone compound has a redox potential of less than −300 millivolts.

16. The absorbent article of claim 11, wherein said high-surface area particles comprise a pore volume of less than 0.5 milliliters per gram.

17. The absorbent article of claim 16, wherein said high-surface area particles have a positive zeta potential.

18. The article of claim 1, wherein the odor control composition is configured to adsorb at least 25% of an odorous compound as determined by the Headspace Gas Chromatography test.

19. The article of claim 1, wherein the odor control composition is configured to adsorb at least 45% of an odorous compound as determined by the Headspace Gas Chromatography test.

20. The article of claim 1, wherein the odor control composition is configured to adsorb at least 65% of an odorous compound as determined by the Headspace Gas Chromatography test.

21. The absorbent article of claim 11, wherein the odor control composition is configured to adsorb at least 25% of an odorous compound as determined by the Headspace Gas Chromatography test.

22. The absorbent article of claim 11, wherein the odor control composition is configured to adsorb at least 45% of an odorous compound as determined by the Headspace Gas Chromatography test.

23. The absorbent article of claim 11, wherein the odor control composition is configured to adsorb at least 65% of an odorous compound as determined by the Headspace Gas Chromatography test.

* * * * *